United States Patent [19]

Babb et al.

[11] Patent Number: 5,489,623

[45] Date of Patent: Feb. 6, 1996

[54] PHOTODEFINABLE POLYMERS CONTAINING PERFLUOROCYCLOBUTANE GROUPS

[75] Inventors: David A. Babb; W. Frank Richey; Katherine S. Clement, all of Lake Jackson, Tex.; Eric S. Moyer, Midland, Mich.; Marius W. Sorenson, Lake Jackson, Tex.

[73] Assignee: The Dow Chemical Company, Midland, Mich.

[21] Appl. No.: 428,740

[22] Filed: Apr. 25, 1995

Related U.S. Application Data

[62] Division of Ser. No. 996,452, Dec. 24, 1992, Pat. No. 5,426,164.

[51] Int. Cl.$^6$ .................................................. C08F 2/48
[52] U.S. Cl. ..................... 522/151; 522/152; 522/153; 522/154; 522/156; 427/508; 427/510; 427/520
[58] Field of Search .................................. 522/151, 152, 522/153, 154, 156; 427/508, 510, 520

[56] References Cited

U.S. PATENT DOCUMENTS

| | | |
|---|---|---|
| 3,453,237 | 7/1969 | Borden et al. . |
| 3,647,444 | 3/1972 | Borden et al. . |
| 5,021,602 | 6/1991 | Clement et al. . |
| 5,023,380 | 6/1991 | Babb et al. . |
| 5,037,917 | 8/1991 | Babb et al. . |
| 5,037,918 | 8/1991 | Babb . |
| 5,037,919 | 8/1991 | Clement et al. . |
| 5,066,746 | 11/1991 | Clement et al. . |
| 5,084,538 | 1/1992 | Suzuki et al. . |
| 5,159,036 | 10/1992 | Babb . |
| 5,159,037 | 10/1992 | Clement et al. . |
| 5,159,038 | 10/1992 | Babb et al. . |
| 5,162,468 | 11/1992 | Babb et al. . |

FOREIGN PATENT DOCUMENTS

| | | |
|---|---|---|
| 0115471 | 8/1984 | European Pat. Off. . |
| 0490335A2 | 6/1992 | European Pat. Off. . |
| 91/18859 | 12/1991 | WIPO . |

OTHER PUBLICATIONS

Chemical Abstract 103: 45821e, 1985.
Chemical Abstract 96: 218715r, 1982.
Chemical Abstract 92: 199109v, 1980.
Chemical Abstract 91: 124401e, 1979.
Chemical Abstract 89: 138345k, 1978.
Chemical Abstract 88: 191835a, 1978.
Chemical Abstract 111: 173458u, 1989.
Chemical Abstract 106: 58785h, 1987.
Chemical Abstract 86: 113723g, 1977.
Chemical Abstract 70: 20691z, 1969.
Douglas G. Borden, *ACS Div. Org. Coat. Plast. Chem. Pap.*, vol. 35, pp. 96–101, (1975), "Changes in Photosensitivity".
*Journal of Polymer Science*: Part A, vol. 2, pp. 2907–2916, 1964, "Some Aspects of the Photosensitivity of Poly(vinyl Cinnamate)."C. G. Roffey, *Photopolymerization of Surface Coatings*, (1982), pp. 26–27, 67–68, 141–161, 276–283, 290–296.
H. J. Merrem et al, *Polyimides*, vol. 2, pp. 919–931, (1984) "New Developments in Photosensitive". Polyimides.
O. Rohde, *Advances in Resist Technology and Processing II*, vol. 539, pp. 175–179, (1985), "Recent Advances in Photoimagable Polyimides".
*Journal of Polymer Science*: Part A–1, vol. 8, pp. 1939–1948, (1970), "Photocycloaddition Polymerization I. Preparation and Characterization of Poly–N, N'–polymethylenebisdichloromaleimides*".
*Journal of Polymer Science*: Part A–1, vol. 8, pp. 1022–1023, (1970), "Photosensitization of Polyacetylenes".
EM Industries, Inc., *Merck Electronic Chemicals*, "Photoresists", pp. 1–31.
L. F. Thompson et al., *ACS Symposium Series* 219, pp. 43–46, 90–92, 107–159, (1983) "Introduction to Microlithography".
Elsa Reichmanis et al, *ACS Symposium Series* 412, pp. 1–24, (1989), "Polymers in Microlithography".
Derwent Abstract 84–196843/32.

*Primary Examiner*—Bernard Lipman

[57] ABSTRACT

A polymer has at least one photoactive site and more than one perfluorocyclobutane group. New monomers containing photoactive sites or photoactive precursors and at least one perfluorovinyl group are useful for making such polymers. Processes of making such polymers and the monomers from which they are made are disclosed. The polymers are useful in coatings, photoresists, and the like.

47 Claims, No Drawings

PHOTODEFINABLE POLYMERS CONTAINING PERFLUOROCYCLOBUTANE GROUPS

CROSS-REFERENCE TO RELATED APPLICATION

This is a divisional of application Ser. No. 0/996,452 filed Dec. 24, 1992 now U.S. Pat. No. 5,462,164.

This invention relates to photoimageable polymers, particularly those polymers having perfluorocyclobutane groups.

Photoimageable polymers are widely used, especially in the electronics industry to apply coatings of polymer to exact portions of an electronic device, often such that other materials, for instance metals can be applied in regions not coated with polymer. There are a number of ways of achieving the desired results, conveniently classified into positive photoresists, in which the area exposed to light is removed, and negative photoresists, in which the area exposed to light is insolubilized and remains after the unexposed area is removed.

Polyimide negative photoresists are widely used in electronics. Because most polyimides are nearly insoluble in common organic solvents, a soluble precursor is generally used. The precursor has a photosensitive group such as a methacrylate ester group. The photosensitive group results in crosslinking of the precursors on exposure to light of a certain wavelength, such that unexposed precursor can be removed by solvent washing. Then the remaining precursor is converted to polyimide by exposure to heat of about 400° C. Exposure to such heat results in loss of the photosensitive groups and water. Loss of such materials requires removal of them and often results in bubbles and shrinkage of from about 15 to about 50 percent. Photodefinable polyimides that are not subjected to a high temperature post-cure contain unreacted polyamic acid groups that contribute to increases in the dielectric constant and water absorption of the polymer. Such systems are described in references such as Rohde et al. "Recent Advances in Photoimageable Polyimides," SPIE Vol. 539 *Advances in Resist Technology and Processing II* (1985).

Those skilled in the art recognize that polyimides, though widely used have various disadvantages. For instance, D. Makino has stated, Though many kinds of photosensitive polyimides, including positive working or preimidized, have been proposed, their processing latitudes are narrow and their properties are still inferior to thermal cure polyimides, and their application has been limited to a small portion of microelectronics.

"Recent Progess of the Application of Polyimides to Microelectronics", Proceedings of the American Chemical Society Division of Polymeric Materials: Science and Engineering, vol. 66, April 1992, p. 233.

Furthermore, when the optical density of the photosensitive material is high in the region of excitation and does not show a hypsochromic shift when irradiated, then most of the photochemistry will occur on the surface. Light intensity will be significantly attenuated and thus the level of crosslinking will be decreased as a function of depth into the photosensitive layer. This results in undercutting of pattern features and creates problems in line width control and integrated circuit fabrication.

A number of other polymers have been suggested for use as photoimageable polymers; however, they have not offered properties suitable for use in electronics. For instance, certain photoimageable polyesters disclosed by J. G. Jegal, L. H. Lin and A. Blumstein, Polymer Preprints, Vol. 32, No. 3, August 1991, pp. 205–206, were formed by reaction of 4,4'-Dihydroxy-α-methylstilbene with various dicarboxylic acids, and subsequently crosslinked via irradiation with UV light at 254 nm. The resulting polyesters have not been used in thin film dielectric or microelectronic applications because polyesters in general exhibit relatively higher water absorption and dielectric values than polymers currently used in these applications.

It would be desirable to have a photoimageable polymer which does not lose water or other materials in its formation or insolubilization, and therefore has less resulting shrinkage, which does not require heating to 300° or 400° C., shows a hypsochromic or bathochromic shift (that is a shift of the absorption maxiumum to shorter or longer wavelengths respectively) when irradiated and which has properties such as low dielectric constant, low dissipation factor, low moisture absorbance, low ionic mobility or ionic transport properties, optical clarity (to visible light) good planarizability, good compatibility of the prepolymer with a wide variety of organic solvents (such as ethers, ketones, aromatics, that is, compounds containing a benzene ring, either substituted or unsubstituted, including fused ring systems such as naphthalene, as is described by Andrew Streitwieser, Jr. and Clayton Heathcock in *Introduction to Organic Chemistry*, Macmillan Publishing Co., Inc., 1976, p. 35 and p. 577, polar aprotics and the like to facilitate application methods such as spin coating, spray coating, dip coating, roll coating, pad printing and the like, but after thermal curing and/or no curing yields a finished polymer with good solvent resistance and good resistance to chemical etchants such as acids and bases.

SUMMARY OF THE INVENTION

In one aspect the invention is a polymer having at least one photoactive site and more than one perfluorocyclobutane group. The invention also includes monomers containing photoactive sites or photoactive precursors for making such polymers.

In another aspect, the invention includes the uses of such polymers in coatings and in negative photoresists.

In yet another aspect the invention includes processes of making such polymers and the monomers from which they are made.

DETAILED DESCRIPTION OF THE INVENTION

Polymers of the invention have at least one photoactive site, that is a grouping of atoms capable of absorbing energy from incident photonic radiation such that the polymer becomes less soluble or dispersible in at least one solvent or dispersing medium than it was before exposure to the incident photonic radiation. Compounds of the invention also have such photoactive sites or photoactive precursors; in which case, a polymer made at least partially from such compounds containing photoactive sites becomes less soluble or dispersible upon photonic irradiation. Decreasing solubility or dispersibility is also evidenced by differential solubility between exposed and unexposed polymer, for example in a layer, a first portion of which is exposed to incident photonic radiation and second portion of which remains unexposed.

The term "incident photonic radiation" or "actinic radiation" refers to energy in the form of electromagnetic waves of a wavelength capable of exciting bonding or non-bonding electrons in certain functional groups referred to herein as photoactive sites or the active portion of such sites to produce a chemical reaction.

The term polymer is used herein to include any compound or compounds comprised of two or more like or different monomer units. Thus the term polymer includes prepolymers, dimers, trimers, tetramers and other oligomers.

Determining reduced solubility or dispersibility is within the skill in the art. For instance, a solid, gel, or organic phase separates from a liquid medium; more solvent is required to dissolve or disperse the same weight of polymer; latex particles coalesce; an emulsion separates or requires additional stirring. The polymer is optionally dissolved or dispersed in any medium effective therefor. For instance, polymers of the invention are advantageously dissolved in solvents such as ethers, ketones, aromatic hydrocarbons, polar aprotic solvents, halocarbon solvents and the like. Among these solvents, mesitylene, diglyme, n-methylpyrrolidinone, and dimethylformamide are advantageously used in electronic applications such as depositing a layer of polymer on a substrate such as a metal (e.g. copper, aluminum, indium, tin, silver, gold, platinum, cadminum and alloys thereof), silicon, silicon oxide, gallium arsenide, germanium arsenide, barrium ferrite, alloy of chromium and at lest one other metair ceramitized glass, indium tin oxide, glass, quartz, a like, similar, or different polymer (particularly epoxy resins, polycarbonates, polyesters, polyimides, polystyrenes (particularly syndiotactic), benzocyclobutenes, acrylics, other perfluorocyclobutane-containing polymers having different aryl groups and combinations thereof), graphite, combinations of the above and the like. Similarly, the polymer may be dispersed in an aqueous and/or organic medium particularly in an aqueous medium. For instance, in the form of a latex or emulsion. Reduced solubility or dispersibility is believed to be associated with increased molecular weight of the polymer, for instance from increasing chain length, or preferably crosslinking. Preferably, the decreased solubility or dispersibility is a result of chemical changes (chemical reactions), which more preferably result in the formation of covalent bonds. Formation of coatings and other layers of this type of polymer is advantageously as disclosed in U.S. application Ser. No. 07/792,553 (C-39, 066) filed Nov. 15, 1991, which is incorporated herein by reference.

Polymers of the invention additionally have more than one perfluorocyclobutane group. Methods of making polymers having perfluorocyclobutane groups are disclosed in U.S. Pat. Nos. 5,021,602; 5,023,386; 5,037,917, 5,037,918 and 5,037,919 which are incorporated herein by reference in their entireties. U.S. Pat. No. 5,021,602 (Clement et al.) discloses compounds of the formula:

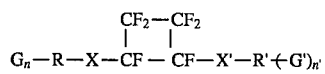

(hereinafter Formula I)
wherein R and R' independently represent optionally inertly substituted hydrocarbyl groups; X and X' represent any molecular structures which link R and R' with the perfluorocyclobutane ring; n and n' are the number of G and G' groups, respectively; and G and G' independently represent any reactive functional groups or any groups convertible into reactive functional group and methods for making such compounds and forming polymers therefrom.

U.S. Pat. No. 5,023,380 (Babb et al) discloses compounds of the formula:
(hereinafter Formula II)

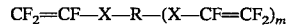

wherein R represents an unsubstituted or inertly substituted hydrocarbyl group; each X is independently selected from the group consisting of groups having at least one non-carbon atom between R and —CF=CF$_2$; and m is an integer of from 1 to about 3 and methods for making such compounds and forming polymers therefrom.

U.S. Pat. No. 5,037,919 (Clement, et al.) discloses compounds of the formula:

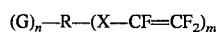

(hereinafter Formula III)
wherein R represents an optionally substituted hydrocarbyl group, X represents any group which links R and a trifluorovinyl (perfluorovinyl, trifluoroethenyl, or perfluoroethenyl) group; n is the number of G groups, m is the number of (XCF=CF$_2$) groups; and G represents any reactive functional group or a group convertible into a reactive functional group and methods for making such compounds and forming polymers therefrom.

These patents and U.S. Pat. No. 5,037,917 (Babb et al.) and U.S. Pat. No. 5,037,918 (Babb) all of which are incorporated herein by reference in their entireties disclose preferably, for polymers having good plastic properties such as tensil strength and flexibility; at least one carbon atom of R is in the molecular claim between X's and is part of an aromatic nucleus, and methods of forming polymers having perfluorocyclobutane rings by heating monomers having trifluorovinyl groups, by reacting compounds having perfluorocyclobutane groups such as compounds of Formula I with di- or polyfunctional compounds reactive with the groups designated G and/or G'; and by reacting compounds having a reactive group (G) and at least one trifluorovinyl group such as compounds of Formula III with oligomers or polymerizable compounds followed by polymerization.

The disclosed methods are applicable for forming polymers of the invention. In the practice of the present invention, however; at least a portion of the compounds used in forming the polymers have photoactive sites. In the practice of the invention R and R' preferably have from about 6 to about 100 carbon atoms, more preferably from about 6 to about 50 carbon atoms, most preferably from about 6 to about 25 carbon atoms. For instance, the molecular fragments designated R and R' in Formulas I–III optionally have photoactive sites. Photoactive sites include those having at least two conjugated multiple bonds (wherein the term "multiple bonds" is used to include double, triple or aromatic bonds between two carbon atoms, between a carbon atom and a heteroatom such as an oxygen, nitrogen, sulfur, phosphorus or between two or more heteroatoms such as between sulfur and oxygen, phosphorus and oxygen or sulfur, nitrogen and oxygen, or nitrogen and nitrogen such that incident photonic radiation is absorbed by the molecule.

Exemplary photoactive sites include molecular groups such as:

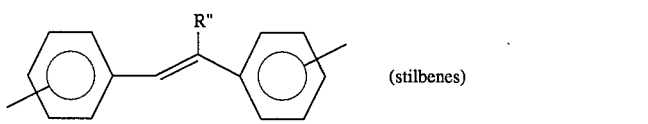 (stilbenes)
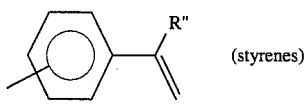 (styrenes)
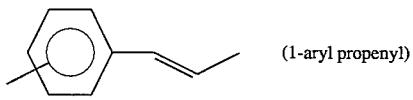 (1-aryl propenyl)
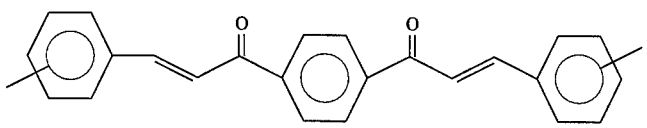 (bischalcone, o, m, or p substituted)
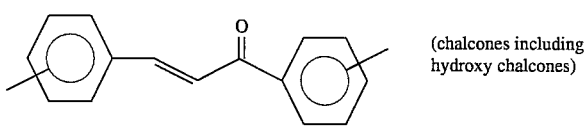 (chalcones including hydroxy chalcones)
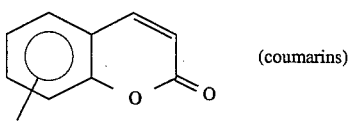 (coumarins)
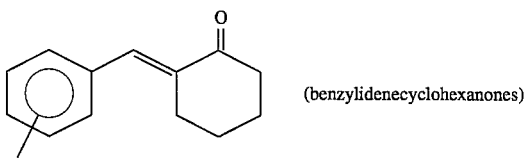 (benzylidenecyclohexanones)
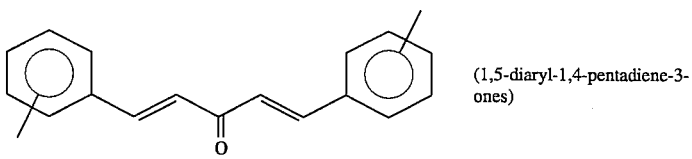 (1,5-diaryl-1,4-pentadiene-3-ones)
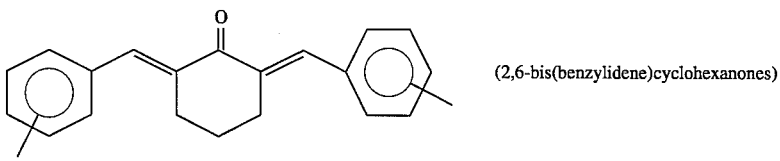 (2,6-bis(benzylidene)cyclohexanones)
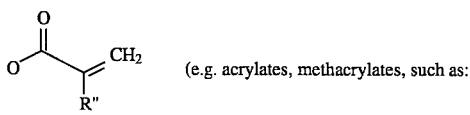 (e.g. acrylates, methacrylates, such as:
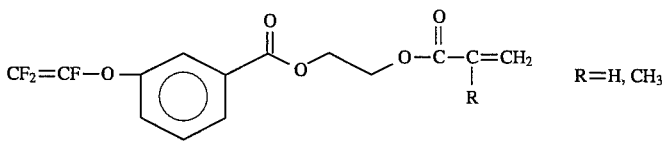 R=H, CH$_3$
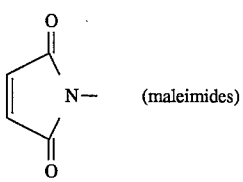 (maleimides)

-continued

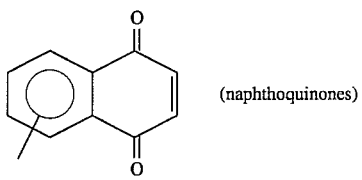
(naphthoquinones)

(polyacetylenes)

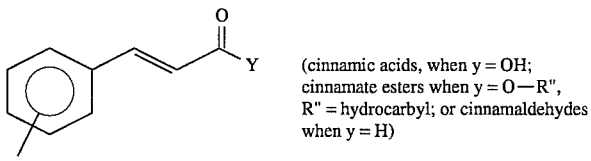
(cinnamic acids, when y = OH;
cinnamate esters when y = O—R",
R" = hydrocarbyl; or cinnamaldehydes
when y = H)

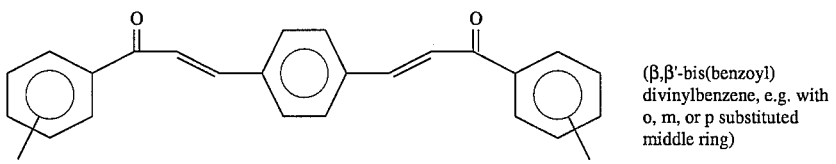
(β,β'-bis(benzoyl)
divinylbenzene, e.g. with
o, m, or p substituted
middle ring)

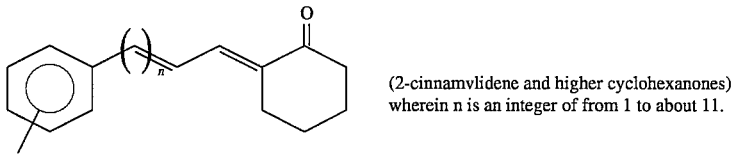
(2-cinnamylidene and higher cyclohexanones)
wherein n is an integer of from 1 to about 11.

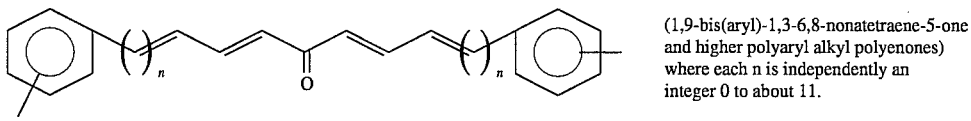
(1,9-bis(aryl)-1,3-6,8-nonatetraene-5-one
and higher polyaryl alkyl polyenones)
where each n is independently an
integer 0 to about 11.

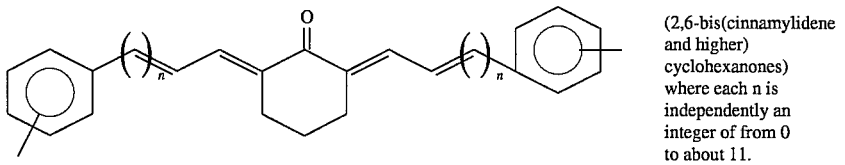
(2,6-bis(cinnamylidene
and higher)
cyclohexanones)
where each n is
independently an
integer of from 0
to about 11.

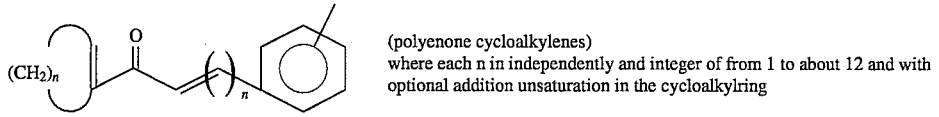
(polyenone cycloalkylenes)
where each n in independently and integer of from 1 to about 12 and with
optional addition unsaturation in the cycloalkylring

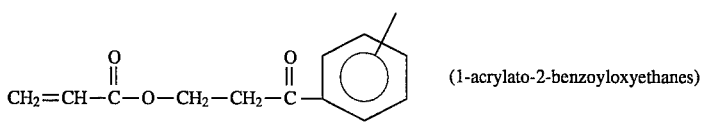
(1-acrylato-2-benzoyloxyethanes)

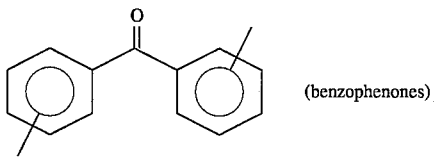
(benzophenones)

in each case wherein each R" is H or a hydrocarbyl group which is optionally inertly substituted, preferably H or a hydrocarbyl group of from 1 to about 12 carbon atoms, more preferably H or an alkyl hydrocarbyl group of from to about 6 carbon atoms; and Y stands for a bond to any other atom or group of atoms (e.g. H, OH, OR, R", SH, SR", NHR", and the like). Any photoactive site or compound containing such a site is optionally inertly substituted, that is substituted with any group which does not undesirably affect the function of the photoactive site.

The photoactive site (represented hereinafter as "PAS") is optionally any part of a compound and optionally becomes part of a polymer backbone or side chain. For instance, when the photoactive site corresponds to at least a portion of R in Formula II, a monomer is represented:

$$CF_2=CF-X-PAS-(X-CF=CF_2)_q$$

(Formula IV)

wherein X is as defined for Formula I; PAS is a photoactive site or photoactive precursor as defined previously; and q is an integer of from 0 to about 4. When such a compound is polymerized by formation of perfluorocyclobutane groups from the trifluorovinyl groups, the photoactive sites are in the polymer backbone. Alternatively, the photoactive sites are in side chains such as when a compound such as $$CF_2=CF_2-X-\underset{(PAS)_r}{R''}-(X-CF=CF_2)_q \qquad \text{(Formula V)}$$

wherein X is as defined for Formula I; R" is as defined for R and R' of Formula I except that it is substituted with PAS which is as defined for Formula IV; q is an integer of from 0 to about 4; and r is an integer from 1 to about 4 is similarly polymerized. Compounds of Formula IV or V are novel compounds of the invention.

Alternatively, photoactive sites are formed on already formed polymers having plural perfluorocyclobutane groups, such as by reaction of compounds having photoactive sites or photoactive precursors that are subsequently converted to photoactive sites with any polymer formed by a process taught in any of the already cited patents disclosing perfluorocyclobutane containing polymers.

When the polymer of the invention is formed at least partially from compounds corresponding to Formulas I, II or III wherein R and/or R' contain at least one photoactive site (as in Formula IV or V), the compounds are suitably formed by methods disclosed in the cited references from starting materials having the desired photoactive site(s) or from starting materials having precursors for the photoactive sites. When zinc is used to form trifluorovinyl groups from bromotetrafluoroethyl groups, it is preferable to use precursors for photoactive sites containing carbon-carbon double bonds conjugated with aromatic rings and carbon-oxygen double bonds because such double bonds are often attacked by zinc under reaction conditions. For instance, paraperfluoroethenyloxybenzaldehyde can be formed by reaction of zinc with parabromotetrafluoroethoxybenzaldehyde; then for instance, the para-perfluoroethenyloxybenzaldehyde can be condensed in an aldol condensation with a ketone, either two moles of the aldehyde with a ketone like acetone or one mole of the aldehyde with a trifluoroethenyl compound containing a ketone group e.q. paraperfluoroethenyloxyacetophenone to form

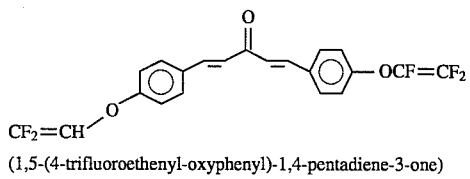

(1,5-(4-trifluoroethenyl-oxyphenyl)-1,4-pentadiene-3-one)

or

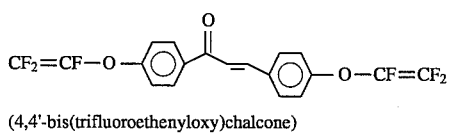

(4,4'-bis(trifluoroethenyloxy)chalcone)

respectively.

A process for making such compounds is then:

(a) forming a salt having an anion corresponding to a compound (acid) of Formula VI:

$$HX-\underset{VI}{PAP}-(XH)_q$$

wherein X and q are defined as for Formula IV; and PAP and PAP' are photoactive precursors (any group(s) which can react to form a photoactive group), where PAP represents a group which can be modified to become photoactive (either a single group or a group illustrated by the benzaldehyde and acetophenone groups in the above illustration which can react, optionally with other reactants, to become a photoactive site);

(b) reacting the salt with a 1,2-dihalo-1,1,2,2-tetrafluoroethane wherein the halo groups are iodine, bromine, chlorine or mixtures thereof, at least one halo group being a bromine or an iodine atom, to form a compound of Formula VII;

$$Z-CF_2CF_2-X-PAP-(X-CF_2CF_2-Z)_q \qquad VII$$

wherein PAP, X and q are defined as for Formula VI; and each Z is independently iodine or bromine;

(c) eliminating the halogen atoms represented by Z to form the trifluorovinyl compound (s); and $$CF_2=CF-X-PAP-(X-CF=CF_2)_q \qquad VIII$$

wherein X, PAP, and q are as defined for Formula VI.

(d) modifying the photoactive precursors (PAP) to form photoactive sites (PAS) to form compounds represented by Formula IV.

$$CF_2=CF-X-PAS-(X-CF=CF_2)_q$$

Step d is suitably before or after step(s) b and/or c. Those skilled in the art are able to ascertain suitable order of steps from chemical sensitivity and reactivities of groups present with reactants used in the steps.

It should be noted that groups represented by PAP, and PAS optionally include groups which are not photoactive along with the photoactive groups. For instance the molecular structure between the X's in Formula IV is optionally not itself totally photoactive but has, for instance a pendant photoactive group or a reactive group to which a photoactive site may be attached.

The step of modifying the photoactive precursor(s) optionally includes reactions which combine like or different precursors to form a photoactive site as illustrated by the condensation of aldehydes and ketones already discussed. Alternatively, one site in a molecule is chemically modified. For instance, a photoactive site of unsaturation (carbon-carbon double bond) may be generated from a non-photoactive precursor by the acid catalyzed α, β-dehydration of an alkyl alcohol. Alternatively, a photoactive site may be modified via reactive substitution to change the quantum yield or absorption maximum of the chromophore. For instance, the compound 4-(trifluoroethenyloxy)-β-( 4-nitrobenzylidene) acetophenone, formed by the Aldol condensation of 4-(trifluoroethenyloxy)acetophenone with 4-nitrobenzaldehyde, is suitably catalytically hydrogenated using palladium on carbon to reduce the nitro group to an amine, thereby changing the absorption spectrum of the chromophore. The resulting amine is optionally subsequently reacted with iodomethane to form the dimethylamine compound to further change the absorption characteristics of the chromophore.

Steps (a) through (c) of the process are advantageously carried out as described in U.S. Pat. No. 5,023,380.

Compounds of Formula IV where q is at least 1 are homo or copolymerized to form polymers having photoactive sites and perfluorocyclobutane groups.

In a variation on this process, a compound of Formula VI where q is 0 is used to form a compound of Formula IV where q is 0 and wherein the molecular structure represented by PAP includes a group reactive with at least one compound to become a photoactive site. The compound $CF_2=CF-X-PAP$ has one trifluorovinyl group which is reacted into perfluorocyclobutane-containing polymers (by processes such as those disclosed in U.S. Pat. Nos. 5,037,917 and 5,037,918), which polymers then have side chains corresponding to molecular structures represented by PAP. Exemplary of compounds of Formula VI where q is 0 are p-perfluoroethenyloxyacetophenones (optionally substituted for instance with cyano, nitro, sulfonate ester, sulfonamide, trifluoromethyl, carboxylic ester, aldehyde, ketone, or halo (preferably fluoro, bromo or chloro) groups in the ortho and/or meta positions) which are reactive, for instance under acid conditions (including hydrochloric acid in ethanol) with optionally substituted benzaldehydes. Such electron donating substituents as methoxy, ethoxy, or dimethylamino, groups para to an aldehyde or propenaldehyde group act to move the wavelength of light absorbed by the resulting chalcone group from about 300–320 nm to 340–420 nm wavelengths, for instance about 414 nm in the case of the p-dimethylamino substituted aldehyde. Electron releasing groups such as secondary or tertiary amines, hydroxy groups, ethers, alkoxy groups preferably of from one to about 12 carbon atoms or alkyl groups preferably having from 1 to about 12 carbon atoms, on the benzaldehyde act to further induce charge separation and cause the resulting compound to absorb light at longer wavelengths. Benzaldehyde is illustrative of aldehydes useful in the process; such aldehydes include unsubstituted or inertly substituted, cinnamaldehydes, acroleins, furfural, heptadienals (and other polyene aldehydes), retinals, phenyl-2,4-pentadienal terephthaldehyde, naphthalenedicarboxaldehyde, furylpolyene aldehydes and combinations thereof.

In yet another variation of the process, a compound of Formula VI where q is 0 is reacted with a compound having at least two, preferably at least three, trifluorovinyl groups such that a perfluorocyclobutane group is formed in a compound having at least one, preferably at least two, more preferably two, trifluorovinyl groups for subsequent polymer formation. Such compounds include reaction products of 1,1,1-tris (4'-trifluoroethenyloxyphenyl) ethane with compounds of Formula IV such as 1-acroyloxy-2-( 4-trifluoroethenyloxy)-benzoyloxyethane and 1-methacroyloxy-2-(4-triifluoroethenyloxy)-benzoyloxyethane and the like.

Similarly, compounds of Formula III are advantageously formed by the process disclosed in U.S. Pat. No. 5,037,919 wherein R contains a photoactive site or by a modification of that process wherein steps a' through c' are advantageously carried out as described therein and step d' involves formation of the photoactive site:

(a') preparing a 2-halotetrafluoro compound of the Formula IX $$(Q-CF_2-CF_2-X-)_m-PAP-(G'')_n$$

or at least two compounds, at least one of each of Formula X and XI $$(Q-CF_2-CF_2-X)_m-PAP' \quad\quad X$$

and $$PAP'-(G'')n \quad\quad XI$$

wherein X, PAP, m and n are as defined for Formulas I and II, and Q is bromine, chlorine or iodine: and G" is a functional group G; as previously defined, or a functional group suitable for conversion into G: and each PAP' is independently the same or different photoactive precursor which react with one another to form a photoactive site;

(b') chemically modifying group G" to produce functional group G;

(c') dehalogenating the 2-halotetrafluoro compound to form the corresponding trifluorovinyl compound; and (d') modifying the photoactive precursors to form photoactive sites thus forming novel compounds of the invention represented by Formula XII:

$$(G)_n-PAS-(X-CF=CF_2)m$$

Step d' is carried out as step d in the process for making compounds of Formula VIII and optionally takes place between steps a' and b', b' and c', after c', or simultaneously with steps b' or c', but preferably after step c'. Also, step b' may take place before or after step c' or step d': For instance; the hydroxy group of β-(4-hydroxybenzylidene )-4-trifluoroethenyloxyacetophenone may be converted to an acetate by treatment with acetyl chloride in tetrahydrofuran.

Exemplary of compounds of Formula XII are β-( 4-hydroxybenzylidene)-4-(trifluoroethenyloxy)acetophenone, β-(4-Acetylbenzylidene)-4-(trifluoroethenyloxy)acetophenone, β-(4-Acetyloxybenzylidene)-4-(trifluoroethenyloxy) acetophenone, β-(4-aminobenzylidene)-4-(trifluoroethenyloxy)acetophenone, β-(4-carboxybenzylidene)-4-(trifluoroethenyloxy)acetophenone, β-(4-isocyanatobenzylidene)-4-(trifluoroethenyloxy)acetophenone, β-(4-chlorocarboxybenzylidene)-4-(trifluoroethenyloxy)acetophenone, β-(4-carboxymethylbenzylidene)-4-(trifluoroethenyloxy)acetophenone, β-(4-carboxyethylbenzylidene)-4-(trifluoroethenyloxy)acetophenone, 4-hydroxy-β-(4-trifluoroethenyloxybenzylidene)acetophenone, 4-amino-β(4-trifluoroethenyloxybenzylidene)acetophenone, 4-carboxy-β-(4-trifluoroethenyloxybenzylidene)acetophenone, 4-chlorocarboxy-β-(4-trifluoroethenyloxybenzylidene)acetophenone, 4-isocyanato-β-(4-trifluoroethenyloxybenzylidene)acetophenone, 4-carboxymethyl-β-(4-trifluoroethenyloxybenzylidene)acetophenone, 4-carboxyethyl-β-4-(trifluoroethenyloxybenzylidene)acetophenone, 1-(4-hydroxyphenyl)-2-(4-trifluoroethenyloxyphenyl)-1-propene, 2-(4-hydroxyphenyl)-1-( 4-trifluoroethenyloxyphenyl)-1-propene, 1-(4-aminophenyl)2-(4-trifluoroethenyloxyphenyl)-1-propene, 2-( 4-aminophenyl)-1-(4-trifluoroethenyloxyphenyl)-1-propene, 1-(4-carboxyphenyl)-2-(4-trifluoroethenyloxyphenyl)-1-propene, 2-(4-carboxyphenyl)-1-(4-trifluoroethenyloxyphenyl)-1-propene, 1-(4-chlorocarboxyphenyl)-2-(4-trifluoroethenyloxyphenyl)-1-propene, 2-(4-chlorocarboxyphenyl)-1-(4-trifluoroethenyloxyphenyl)-1-propene, 1-(4-isocyanatophenyl)-2-(4-trifluoroethenyloxyphenyl)-1-propene, 2-(4-isocyanatophenyl)-1-(4-trifluoroethenyloxyphenyl)-1-propene, 1-(4-carboxymethylphenyl)-2-(4-trifluoroethenyloxyphenyl)-1-propene, 2-(4-carboxymethylphenyl)-1-( 4-trifluoroethenyloxyphenyl)-1-propene, 4-hydroxy-4'-trifluoroethenyloxystilbene, 4-aminophenyl-4'-trifluoroethenyloxystilbene, 4-carboxyphenyl- 4'-trifluoroethenyloxystilbene, 4-isocyanato- 4'-trifluoroethenyloxystilbene, 4-carboxymethyl- 4'-trifluoroethenyloxystilbene, 5-hydroxy- 8-trifluoroethenyloxynaphthoquinone, 1-(4-hydroxyphenyl)-5-(4-trifluoroethenyloxyphenyl)-1,4-pentadien-3-one, 1-(4-aminophenyl)-5-(4-trifluoroethenyloxyphenyl)-1,4-pentadien-3-one, 1-(4-carboxyphenyl)-5-( 4-trifluoroethenyloxyphenyl)-1,4-pentadien-3-one, 1-( 4-carboxymethylphenyl) -5-(4-trifluoroethenyloxyphenyl)-1,4-pentadien-3-one, 1-(4-isocyanatophenyl)-5-( 4-trifluoroethenyloxyphenyl)-1,4-pentadien-3-one, 5-hydroxy-8-trifluoroethenyloxycoumarin, 8-hydroxy- 5-trifluoroethenyloxycoumarin,5-amino- 8-trifluoroethenyloxycoumarin, 8-amino- 5-trifluoroethenyloxycoumarin, 5-isocyanato- 8-trifluoroethenyloxycoumarin, 8-isocyanato-5-trifluoroethenyloxycoumarin, 2-(4-hydroxybenzylidene )-6-(4-trifluoroethenyloxybenzylidene)cyclohexanone, 2-( 4-hydroxybenzylidene)-6-( 4-trifluoroethenyloxybenzylidene)-4-methylcyclohexanone, 2-(4-aminobenzylidene)-6-( 4-trifluoroethenyloxybenzylidene)cyclohexanone, 2-( 4-aminobenzylidene)-6-(4-trifluoroethenyloxybenzylidene)-4-methylcyclohexanone, 2-(4-carboxymethylbenzylidene)- 6-(4-trifluoroethenyloxybenzylidene)cyclohexanone, 2-( 4-carboxymethylbenzylidene)-6-( 4-trifluoroethenyloxybenzylidene)-4-methylcyclohexanone, 2-(4-isocyanatobenzylidene)-6-(4-trifluoroethenyloxybenzylidene)cyclohexanone, 2-( 4-isocyanatobenzylidene)-6-( 4-trifluoroethenyloxybenzylidene)-4-methylcyclohexanone, 2-(4-chlorocarboxybenzylidene )-6-( 4-trifluoroethenyloxybenzylidene) cyclohexanone, 2-( 4-chlorocarboxybenzylidene)-6-( 4-trifluoroethenyloxybenzylidene)-4-methylcyclohexanone Compounds of Formula XII are optionally dimerized as discussed in U.S. Pat. No. 5,021,602 to form compounds of Formula I. Polymers are formed as described in U.S. Pat. Nos. 5,037,919; 5,021,602; 5,037,917 and 5,037,918, which are incorporated by reference in their entirities.

Alternatively, compounds of Formula XII wherein X is oxygen, PAS=ArC(O)CH=CH—Ar wherein Ar is preferably of from 6 to about 50 carbon atoms, and G is a reactive site such as hydroxyl, amine, carboxylic acid, carboxylic acid halide, cyanate, or isocyanate are reacted (through the group represented by G) with such compounds as alkyl diamines, diols, dicarboxylic acids, dicarboxylic acid halides, phosgene, etc. to form polyesters, polyethers, polycarbonates, polyamides, polyurethanes, and the like end capped with trifluoroethenyloxy groups. These compounds are then heated to cause dimerization of the trifluoroethenyloxy end groups, thereby creating perfluorocyclobutane ring containing polymers with photoactive sites included in the polymer backbone. These polymers are suitably dissolved and applied as coatings by any means within the skill in the art such as spin-coating, roll coating, spray coating, pad printing and the like. The coating is then exposed to light of the appropriate wavelength to crosslink the polymer. This photocuring process crosslinks the exposed polymer and thereby imparts increased solvent resistance, increased mechanical properties, and modified optical properties with respect to the unexposed polymer or prepolymer.

Alternative methods for preparing polymers of the invention include a process of preparing a compound of Formula XIII:

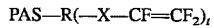

wherein PAS, R, and X are as defined for Formula IV and t is an integer of from 1 to about 4 by (a") forming the salt of an anion corresponding to a compound (acid) of formula XIV:

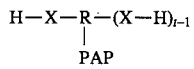

wherein X, R, and t are as defined for Formula XIII and PAP is as defined for Formula VI;

(b") reacting the salt with a 1,2-dihalo-1,1,2,2-tetrafluoroethane wherein the halo groups are iodine, bromine, chlorine or mixtures thereof, at least one halo group being a bromine or an iodine atom, to form a compound of Formula XV:

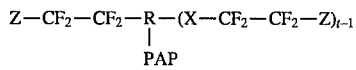

wherein R, X, PAP and t are as defined for Formula XIV are as each Z is independently bromine or iodine (c") eliminating the halogen atoms represented by Z to form the trifluorovinyl compound; and (d") modifying the photoactive precursor to form a photoactive site, forming compounds represented by Formula XIII.

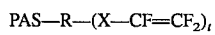

Step (d") is carried out as steps (d) and (d') and optionally occurs before step a" between steps a" and b" or b" and c", simultaneous with steps a", b", or c" or, preferably, after step c". For instance, the acetyl group of 1-(4-acetophenyl)-1,1-bis( 4-trifluoroethenyloxy)phenyl ethane is optionally combined via Aldol condensation with benzaldehyde or variously substituted benzaldehydes to form 1-(4-(β-benzylidene)acetophenyl)- 1,1-bis(4-trifluoroethenyloxy phenyl)ethane.

In an important embodiment of the process of the invention PAP is a molecular structure having a group reactive with at least one compound having or suitable for forming a photoactive site (a photoactive site-containing or photoactive precursor-containing compound). In this embodiment, the step of reacting with such a compound is represented as at least a part of step d". When there are steps of reacting such a PAP with at least one such compound and of converting a resulting PAP into a PAS, the reacting and converting steps are optionally consecutive or separated by one or more of steps B" and c".

Preferred species formed by such a process are compounds of the formula XVI:

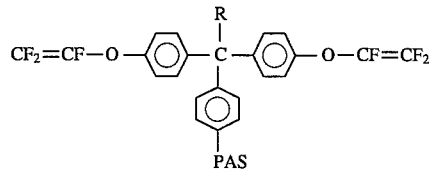

which compounds are novel. Wherein R is an unsubstituted or inertly substituted hydrocarbyl group preferably of from 1 to about 10, more preferably of from 1 to about 4 carbon atoms. R is optionally and advantageously substituted with functional groups which provide additional desirable properties to the polymer, e.g. a photosensitizing group such as those within the skill in the art.

Compounds exemplary of Formula XIII include 1-(4-acroyloxyphenyl)-1,1-bis( 4-trifluoroethenyloxyphenyl)ethane, 1-( 4-methacroyloxyphenyl)-1,1-bis ( 4-trifluoroethenyloxyphenyl)ethane, 1-( 4-acroylphenyl)-1,1-bis(4- trifluoroethenyloxyphenyl)ethane, 1-( 4-methacroylphenyl)-1,1-bis( 4-trifluoroethenyloxyphenyl)ethane, 4-(1,1-bis( 4-trifluoroethenyloxyphenyl)ethyl)-β-(benzylidene)acetophenone, 4-(1,1-bis( 4-trifluoroethenyloxyphenyl)ethyl)-β-( 4-dimethylaminobenzylidene) acetophenone, 4-(1,1-bis( 4-trifluoroethenyloxyphenyl)ethyl)-β- 4-methoxybenzylidene)acetophenone, 4-(1,1-bis( 4-trifluoroethenyloxyphenyl)ethyl)-β- 4-trifluoromethylbenzylidene) acetophenone, 4-(1,1-bis( 4-trifluoroethenyloxyphenyl)ethyl)-β-( 4-carboxymethylbenzylidene) acetophenone, 4-(1,1-bis( 4-trifluoroethenyloxyphenyl)ethyl)-β-( 4-nitrobenzylidene)acetophenone, 4-(1,1-bis( 4-trifluoroethenyloxyphenyl)ethyl)-β-(4-chlorobenzylidene)acetophenone, 4-(1,1-bis( 4-trifluoroethenyloxyphenyl)ethyl)-β-(4-fluorobenzylidene)acetophenone, 4-(1,1-bis( 4-trifluoroethenyloxyphenyl)ethyl)-β-(4-acetylbenzylidene)acetophenone, 4-(1,1-bis( 4-trifluoroethenyloxyphenyl)ethyl)-β-(4-cyanobenzylidene)acetophenone, 4-(1,1-bis( 4-trifluoroethenyloxyphenyl)ethyl)styrene, 4-(1,1-bis( 4-trifluoroethenyloxyphenyl)ethyl)-N-phenyl maleimide, 1-(4-(1,1-bis(4-trifluoroethenyloxyphenyl)ethyl)phenyl)- 5-phenyl-1,4-pentadiene-3-one, 1-(4-(1,1-bis( 4-trifluoroethenyloxyphenyl)ethyl)phenyl)-5-( 4-(dimethylamino)phenyl)-1,4-pentadiene-3-one, 1-(4-( 1,1-bis(4-trifluoroethenyloxyphenyl)ethyl)phenyl)-5-( 4-methoxyphenyl)-1,4-pentadiene-3-one, 1-(4-(1,1-bis( 4-trifluoroethenyloxyphenyl)ethyl)phenyl)-5-( 4-(carboxymethyl)phenyl)-1,4-pentadiene-3-one, 1-(4-( 1,1-bis(4-trifluoroethenyloxyphenyl)ethyl)phenyl)-5-( 4-carboxyethyl)phenyl)-1,4-pentadiene-3-one, 1-(4-( 1,1-bis(4-trifluoroethenyloxyphenyl)ethyl)phenyl)-5-( 4-(trifluoromethyl)phenyl)-1,4-pentadiene-3-one, 1-( 4-(1,1-bis(4-trifluoroethenyloxyphenyl)ethyl)phenyl)-5-( 4-nitrophenyl)-1,4-pentadiene-3-one, 1-(4-(1,1-bis( 4-trifluoroethenyloxyphenyl)ethyl)phenyl)-5-( 4-chlorophenyl)-1,4-pentadiene-3-one, 1-(4-(1,1-bis( 4-trifluoroethenyloxyphenyl)ethyl)phenyl)-5-( 4-fluorophenyl)-1,4-pentadiene-3-one, 1-(4-(1,1-bis( 4-trifluoroethenyloxyphenyl)ethyl)phenyl)-5-( 4-acetophenyl)-1,4-pentadiene-3-one, 1-(4-(1,1-bis( 4-trifluoroethenyloxyphenyl)ethyl)phenyl)-5-( 4-cyanophenyl)-1,4-pentadiene-3-one, 4-(1,1-bis( 4-trifluoroethenyloxyphenyl)ethyl)phenyl acetylene, 4-(1,1-bis(4-trifluoroethenyloxyphenyl)ethyl)phenyl buta-1,3-diyne, 4-(1,1-bis( 4-trifluoroethenyloxyphenyl)ethyl)phenyl hexa- 1,3,5-triyne, 4-(1,1-bis( 4-trifluoroethenyloxyphenyl)ethyl)phenyl octa-1,3,5,7-tetrayne, 4-(1,1-bis( 4-trifluoroethenyloxyphenyl)ethyl)phenyl-1,3,5,7,9-pentayne, 6-(4-(1,1-bis( 4-trifluoroethenyloxyphenyl)ethyl)phenoxy)naphthoquinone, 6-(4-(1,1-bis( 4-trifluoroethenyloxyphenyl)ethyl)phenoxy)coumarin, 7-( 4-(1,1-bis(4-trifluoroethenyloxyphenyl)ethyl)phenoxy)coumarin, 2-( 4-(1,1-bis(trifluoroethenyloxyphenyl)ethyl)benzylidene)cyclohex anone, 2-(4-( 1,1-bis(trifluoroethenyloxyphenyl)ethyl)phenoxy)benzylidene) cyclohexanone, 1-acroyloxy-2-( 4-trifluoroethenyloxy)benzoyloxyethane, 1-methacroyloxy- 2-(4-trifluoroethenyloxy)benzoyloxyethane, N-( 4-trifluoroethenyloxyphenyl)acrylamide, N-( 4-trifluoroethenyloxyphenyl)methacrylamide, 4-trifluoroethenyloxyphenyl acrylate, 4-trifluoroethenyloxyphenyl methacrylate, N-( 4-trifluoroethenyloxyphenyl)maleimide, N-( 4-trifluoroethenyloxybenzoyl)maleimide, β-( 4-methoxybenzylidene)-4-(trifluoroethenyloxy)acetophenone, β-(4-dimethylaminobenzylidene)- 4-(trifluoroethenyloxy)acetophenone, β-( 4-carboxymethylbenzylidene)- 4-(trifluoroethenyloxy)acetophenone, β-( 4-carboxyethylbenzylidene)- 4-(trifluoroethenyloxy)acetophenone, β-( 4-nitrobenzylidene)-4-(trifluoroethenyloxy)acetophenone, β-(4-chlorobenzylidene)- 4-(trifluoroethenyloxy)acetophenone, β-( 4-fluorobenzylidene)-4-(trifluoroethenyloxy)acetophenone, β-(4-acetylbenzylidene)- 4-trifluoroethenyloxy)acetophenone, β-( 4-cyanobenzylidene)-4-(trifluoroethenyloxy)acetophenone, β-(3-trifluoromethylbenzylidene)- 4-(trifluoroethenyloxy)acetophenone, β-( 4-trifluoromethylbenzylidene)- 4-(trifluoroethenyloxy)acetophenone, β-( 4-trifluoroethenyloxybenzylidene)acetophenone, 4-methoxy-β-(4-trifluoroethenyloxybenzylidene)acetophenone, 4-dimethylamino-β-( 4-trifluoroethenyloxybenzylidene)acetophenone, 4-carboxymethyl-β-( 4-trifluoroethenyloxybenzylidene)acetophenone, 4-carboxyethyl-β-( 4-trifluoroethenyloxybenzylidene)acetophenone, 4-chloro-β-(4-trifluoroethenyloxybenzylidene)acetophenone, 4-nitro-β-(4-trifluoroethenyloxybenzylidene)acetophenone, 4-fluoro-β-(4-trifluoroethenyloxybenzylidene)acetophenone, 4-acetyl-β-( 4-trifluoroethenyloxybenzylidene)acetophenone, 4-cyano-β-(4-trifluoroethenyloxybenzylidene)acetophenone, 4-trifluoromethyl-β-( 4-trifluoroethenyloxybenzylidene)acetophenone, 3-trifluoromethyl-β-( 4-trifluoroethenyloxybenzylidene)acetophenone, 4-trifluoroethenyloxycinnamaldehyde, 4-trifluoroethenyloxycinnamic acid, 4-trifluoroethenyloxycinnamic acid, methyl ester, 4-trifluoroethenyloxycinnamic acid, ethyl ester, 4-trifluoroethenyloxycinnamic acid, isopropyl ester, 4-trifluoroethenyloxycinnamic acid, phenyl ester, 1-( 4-trifluoroethenyloxyphenyl)-propene-1-one, 1-( 4-trifluoroethenyloxyphenyl),1-buten-3-one, 5-(trifluoroethenyloxy)naphthoquinone, 6-(trifluoroethenyloxy)naphthoquinone, 5-( 4-(trifluoroethenyloxy)benzoyloxy)naphthoquinone, 6-( 4-(trifluoroethenyloxy)benzoyloxy)naphthoquinone, 5-(trifluoroethenyloxy)coumarin, 6-(trifluoroethenyloxy)coumarin, 7-(trifluoroethenyloxy)coumarin, 8-(trifluoroethenyloxy)coumarin, 5-( 4-(trifluoroethenyloxy)benzoyloxy)coumarin, 6-( 4-(trifluoroethenyloxy)benzoyloxy)coumarin, 7-( 4-(trifluoroethenyloxy)benzoyloxy)coumarin, 8-( 4-(trifluoroethenyloxy)benzoyloxy)coumarin, 2-( 4-trifluoroethenyoxylbenzylidene)cyclohexanone, 1-( 4-trifluoroethenyloxyphenyl)-5-phenyl-1,4-pentadiene- 3-one, 1-(4-trifluoroethenyloxyphenyl)-5-( 4-(dimethylamino)phenyl)-1,4-pentadiene-3-one, 1-( 4-trifluoroethenyloxyphenyl)-5-(4 -methoxyphenyl)- 1,4-pentadiene-3-one, 1-(4-trifluoroethenyloxyphenyl)-5-( 4-(carboxymethyl)phenyl)-1,4-pentadiene-3-one, 1-( 4-trifluoroethenyloxyphenyl)-5-(4 -(carboxyethyl)phenyl)-1,4-pentadiene-3-one, 1-(4-trifluoroethenyloxyphenyl)- 5-(4-(trifluoromethyl)phenyl)-1,4-pentadiene-3-one, 1-( 4-trifluoroethenyloxyphenyl)-5-(3-(trifluoromethyl)phenyl)-1,4-pentadiene-3-one, 1-( 4-trifluoroethenyloxyphenyl)-5-(4-nitrophenyl)- 1,4-pentadiene-3-one, 1-(4-trifluoroethenyloxyphenyl)-5-( 4-chlorophenyl)-1,4-pentadiene-3-one, 1-( 4-trifluoroethenyloxyphenyl)-5-(4-fluorophenyl)- 1,4-pentadiene-3-one, 1-(4-trifluoroethenyloxyphenyl)-5-( 4-acetyphenyl)-1,4-pentadiene-3-one, 1-(4-methoxyphenyl)-2-(4-trifluoroethenyloxyphenyl)-1-propene, 2-( 4-methoxyphenyl)-1-(4-trifluoroethenyloxyphenyl)- 1-propene, 1-(4-dimethylaminophenyl)-2-( 4-trifluoroethenyloxyphenyl)-1-propene, 2-( 4-dimethylaminophenyl)-1-(4-trifluoroethenyloxyphenyl)- 1-propene, 1-(4-carboxymethylphenyl)-2-( 4-trifluoroethenyloxyphenyl)-1-propene, 2-( 4-carboxymethylphenyl)-1-(4-trifluoroethenyloxyphenyl)- 1-propene, 1-(4-chlorophenyl)-2-( 4-trifluoroethenyloxyphenyl)-1-propene, 2-( 4-chlorophenyl)-1-(4-trifluoroethenyloxyphenyl)-1-propene, 1-(4-nitrophenyl)-2-(4-trifluoroethenyloxyphenyl)-1-propene, 2-(4-nitrophenyl)-1-( 4-trifluoroethenyloxyphenyl)-1-propene, 1-( 4-fluorophenyl)-2-(4-trifluoroethenyloxyphenyl)-1-propene, 2-(4-fluorophenyl)-1-(4-trifluoroethenyloxyphenyl)- 1-propene, 1-(4-cyanophenyl)-2-( 4-trifluoroethenyloxyphenyl)-1-propene, 2-(4-cyanophenyl)-1-(4-trifluoroethenyloxyphenyl)-1-propene, 2-( 4-acetylphenyl)-1-(4-trifluoroethenyloxyphenyl)-1-propene, 2-(4-acetylphenyl)-1-(4-trifluoroethenyloxyphenyl)-1-propene, 4-methoxy-4'-trifluoroethenyloxystilbene, 4-dimethylaminophenyl-4'-trifluoroethenyloxystilbene, 4-carboxymethylphenyl-4'-trifluoroethenyloxystilbene, 4-carboxyethylphenyl-4'-trifluoroethenyloxystilbene, 4-nitro-4'-trifluoroethenyloxystilbene, 4-chloro- 4'-trifluoroethenyloxystilbene, 4-fluoro- 4'-trifluoroethenyloxystilbene, 4-cyano- 4'-trifluoroethenyloxystilbene, 4-acetyl- 4'-trifluoroethenyloxystilbene, 4-trifluoromethyl- 4'-trifluoroethenyloxystilbene, 1-(4-dimethylaminophenyl)-5-(4-trifluoroethenyloxyphenyl)-1,4-pentadiene-3-one, 1-(4-methoxyphenyl)-5-(4-trifluoroethenyloxyphenyl)- 1,4-pentadiene-3-one, β-cinnamylidene-4-trifluoroethenyloxyacetophenone, β-( 4'-dimethylaminocinnamylidene)- 4-trifluoroethenyloxyacetophenone, β-( 2'-methoxycinnamylidene)-4-trifluoroethenyloxyacetophenone, β-(4'-methoxycinnamylidene)- 4-trifluoroethenyloxyacetophenone, 4-(1,1-bis( 4-trifluoroethenyloxyphenyl)ethyl)-β-(benzylidene)acetophenone, 4-(1,1-bis( 4-trifluoroethenyloxyphenyl)ethyl)-β -( 4'-methoxybenzylidene)acetophenone, 4-(1,1-bis( 4-trifluoroethenyloxyphenyl)ethyl)-β-( 4'-dimethylaminobenzylidene)acetophenone, 4-(1,1-bis( 4-trifluoroethenyloxyphenyl)ethyl)-β-( 4'-cyanobenzylidene)acetophenone, 4-(1,1-bis( 4-trifluoroethenyloxyphenyl)ethyl)-β-( 4'-nitrobenzylidene)acetophenone, 4-(1,1-bis( 4-trifluoroethenyloxyphenyl)ethyl)-β-(cinnamylidene)acetophenone, 4-(1,1-bis( 4-trifluoroethenyloxyphenyl)ethyl)-β-( 2'-methoxycinnamylidene)acetophenone, 4-(1,1-bis( 4-trifluoroethenyloxyphenyl)ethyl)-β-( 4'-methoxycinnamylidene)acetophenone, 4-(1,1-bis( 4-trifluoroethenyloxyphenyl)ethyl)-β-( 4'-dimethylaminocinnamylidene)acetophenone, 4-(1,1-bis( 4-trifluoroethenyloxyphenyl)ethyl)-β-( 4'-nitrocinnamylidene)acetophenone, 1,1-bis( 4-trifluoroethenyloxyphenyl)-1-(4-(3-(2-furanyl)- 2-propene-1-onyl)phenyl)ethane, 1,1-bis( 4-trifluoroethenyloxyphenyl)-1-(4-(5-(2-furanyl) - 2,4-pentadiene-1-onyl)phenyl)ethane, 3,5-bis(trifluoroethenyloxy) -β-(benzylidene )acetophenone, 3,5 -bis(trifluoroethenyloxy)-β-( 4'-methoxybenzylidene)acetophenone, 3,5-bis(trifluoroethenyloxy)-β-( 4'-dimethylaminobenzylidene)acetophenone, 3,5-is(trifluoroethenyloxy)-β-( 4'-cyanobenzylidene)acetophenone, 3,5-bis(trifluoroethenyloxy)-β-( 4'-nitrobenzylidene)acetophenone, 3,5-bis(trifluoroethenyloxy)-β-(cinnamylidene)acetophenone, 3,5-bis(trifluoroethenyloxy)-β-( 2'-methoxycinnamylidene)acetophenone, 3,5-bis(trifluoroethenyloxy)-β-( 4'-methoxycinnamylidene)acetophenone, 3,5-bis(trifluoroethenyloxy)-β-(4'-dimethylaminocinnamylidene)acetophenone, 3,5-bis(trifluoroethenyloxy)-β-(nitrocinnamylidene)acetophenone, 3,5-bis(trifluoroethenyloxy)-1-(3-(2-(furanyl)-2-propene-1-onyl)benzene, 3,5-bis(trifluoroethenyloxy)-1-(5-( 2-(furanyl)-2,4-pentadiene-1-onyl)benzene, 2-(3-phenyl- 2-propene-1-onyl)-9,9-bis( 4-trifluoroethenyloxyphenyl)fluorene, 2-(3-( 4-methoxyphenyl)-2-propene-1-onyl)-9,9-bis( 4-trifluoroethenyloxyphenyl)fluorene, 2-(3-( 2-methoxyphenyl)-2 -propene-1-onyl)-9,9-bis( 4-trifluoroethenyloxyphenyl)fluorene, 2-(3-( 4-dimethylaminophenyl)-2-propene-1-onyl)-9,9-bis( 4-trifluoroethenyloxyphenyl)fluorene, 2-(3-( 4-cyanophenyl)-2-propene-1-onyl)-9,9-bis( 4-trifluoroethenyloxyphenyl)fluorene, 2-(3-( 4-nitrophenyl)-2-propene-1-onyl)-9,9-bis( 4-trifluoroethenyloxyphenyl)fluorene, 2,7-bis(3-phenyl- 2-propene-1-onyl)-9,9-bis( 4-trifluoroethenyloxyphenyl)fluorene, 2,7-bis(3-( 4-methoxyphenyl)-2-propene-1-onyl)-9,9-bis( 4-trifluoroethenyloxyphenyl)fluorene, 2,7-bis(3-( 2-methoxyphenyl)-2-propene-1-onyl)-9,9-bis( 4-trifluoroethenyloxyphenyl)fluorene, 2,7-bis(3-( 4-dimethylaminophenyl)-2-propene-1-onyl)-9,9-bis( 4-trifluoroethenyloxyphenyl)fluorene,2,7-bis(3-( 4-cyanophenyl)-2-propene-1-onyl)-9,9-bis( 4-trifluoroethenyloxyphenyl)fluorene, 2,7-bis(3-( 4-nitrophenyl)-2-propene-1-onyl)-9,9-bis( 4-trifluoroethenyloxyphenyl)fluorene, 2-(5-phenyl- 2,4-pentadiene-1-onyl)-9,9-bis( 4-trifluoroethenyloxyphenyl)fluorene, 2-(5-( 4-methoxyphenyl)-2,4-pentadiene-1-onyl)-9,9-bis( 4-trifluoroethenyloxyphenyl)fluorene, 2-(5-( 2-methoxyphenyl)-2,4-pentadiene-1-onyl)-9,9-bis( 4-trifluoroethenyloxyphenyl)fluorene, 2-(5-( 4-dimethylaminophenyl)-2,4-pentadiene-1-onyl)-9,9-bis( 4-trifluoroethenyloxyphenyl)fluorene, 2-(5-( 4-cyanophenyl)-2,4-pentadiene-1-onyl)-9,9-bis( 4-trifluoroethenyloxyphenyl)fluorene, 2-(5-( 4-nitrophenyl)-2,4-pentadiene- 1-onyl)-9,9-bis( 4-trifluoroethenyloxyphenyl)fluorene, 2,7-bis(5-phenyl-2,4-pentadiene-1-onyl)-9,9-bis( 4-trifluoroethenyloxyphenyl)fluorene, 2,7-bis(5-( 4-methoxyphenyl)-2,4-pentadiene-1-onyl)-9,9-bis( 4-trifluoroethenyloxyphenyl)fluorene, 2,7-bis(5-( 4-dimethylaminophenyl)-2,4-pentadiene-1-onyl)-9, 9-bis( 4-trifluoroethenyloxyphenyl)fluorene,2,7-bis(5-( 2-dimethylaminophenyl)-2,4-pentadiene-1-onyl)-9,9-bis( 4-trifluoroethenyloxyphenyl)fluorene,2,7-bis(5-( 4-cyanophenyl)-2,4-pentadiene-1-onyl)-9,9-bis( 4-trifluoroethenyloxyphenyl)fluorene,and 2,7-bis(5-(4-nitrophenyl)-2,4-pentadiene-1-onyl)- 9,9-bis(4-trifluoroethenyloxyphenyl)fluorene.

When R is part of PAS and t is 2, compounds of Formula XIII correspond to Formula IV. Exemplary compounds of Formula IV include 4,4'-bis(trifluoroethenyloxy)-α-methylstilbene; 4,4'-bis(trifluoroethenyloxy)stilbene; 4-Trifluoroethenyloxy-β-(4-trifluoroethenyloxybenzylidene)acetophenone; 2,6-bis(4-trifluoroethenyloxybenzylidene)cyclohexanone, 2,6-bis(4-trifluoroethenyloxybenzylidene)- 4-methylcyclohexanone; 1,4-bis(3-( 4-trifluoroethenyloxyphenyl)-2-propene-1-onyl)benzene; 1,3-bis(3-(4-trifluoroethenyloxyphenyl)-2-propene- 1-onyl)benzene; 1,4-bis(3-(4-trifluoroethenyloxyphenyl)- 1-propene-3-onyl)benzene; 1,3-bis(3-( 4-trifluoroethenyloxyphenyl)-1-propene-3-onyl)benzene; 1,5-bis(4-trifluoroethenyloxyphenyl)-1,4-pentadiene-3-one; 4-Trifluoroethenyloxy-β-( 4-trifluoroethenyloxybenzylidene)acetophenone; 4,4'-bis(trifluoroethenyloxy)stilbene; 4,4'-bis(trifluoroethenyloxy)-α-methylstilbene; β,β'-bis( 4-trifluoroethenyloxybenzylidene)-1,4-diacetylbenzene; β,β'-bis(4-trifluoroethenyloxybenzylidene)- 1,3diacetylbenzene; β,β'-bis( 4-trifluoroethenyloxybenzylidene)-1,2-diacetylbenzene; 5,8-bis(trifluoroethenyloxy)coumarin; 2,6-bis(4, trifluoroethenyloxybenzylidene)cyclohexanone; 2,6-bis(4, trifluoroethenyloxybenzylidene)- 4-methylcyclohexanone, 5,8-bis(trifluoroethenyloxy)naphthoquinone; β,β'-bis(4-trifluoroethenyloxybenzoyl)-1,4-divinylbenzene.

Polymers of the invention include those formed according to the teachings of U.S. Pat. No. 5,037,917 by copolymerizing or reacting such compounds with compounds of Formula II wherein m is greater than 1 to form polymers having (in the case of m=2) repeating units of Formula XV:

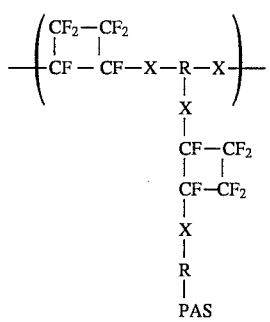

wherein X, R, and PAS are as defined for Formulas I and IV.

For instance, the reaction products of compounds of Formula XIII where t=1 with compounds such as 1,1,1-tris (4'-trifluoroethenyloxyphenyl)ethane, (1,3,5-tris(2-(4-trifluoroethenyloxy)phenylene)-2-propyl benzene), or the (trifluorovinyl etherified) polyphenolic compounds such as Novolac compounds, exemplify polymers of Formula XV. Preferred Novolac compounds correspond to Formula XVI:

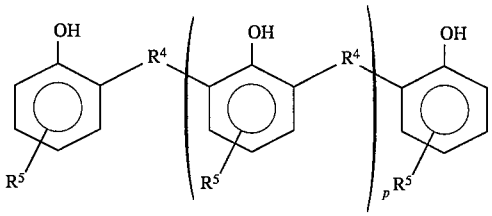

wherein p is an integer of from 0 to about 10; each $R^4$ is independently a linear or cyclic hydrocarbylidene or group preferably of from 1 to about 20 carbon atoms (more preferably methylene, dicyclopentadienylene, isopropylidenelene, fluorenylidene; and the like); and each $R^5$ is independently a hydrogen or an unsubstituted or inertly substituted alkyl or alkyl ether group preferably of from 1 to about 6 carbon atoms, preferably of 1 to about 3 carbon atoms.

Monomers containing trifluorovinyl or perfluorocyclobutane groups and photoactive groups are suitably homopolymerized or copolymerized, preferably copolymerized, for instance, with any monomer of the types disclosed by U.S. Pat. Nos. 5,021,602; 5,023,380; 5,037,917; 5,037,918; or 5,037,919; by methods disclosed therein. Preferably sufficient monomer having at least one photoactive site or photoactive precursor to form a polymer which becomes less soluble or dispersible upon exposure to photonic radiation is used. Advantageously, at least about 0.1 percent by molar composition of such monomers are used in a polymer, preferably at least about 1, more preferably from about 1 to about 100, most preferably from about 5 to about 25 mole percent of photoactive site containing monomers are used. The polymer is suitably linear, branched, crosslinked, or a mixture thereof.

To avoid solubility of at least a portion of a photoactive polymer after treatment with actinic radiation, it is advantageous to avoid having low molecular weight oligomers and polymers after photoactive sites have reacted. When a photoactive monomer containing two trifluorovinyl groups is homopolymerized or copolymerized with another monomer containing two trifluorovinyl groups to form a substantially linear thermoplastic polymer with photoactive sites either pendant to or incorporated in the polymer backbone, the molecular weight of such a system is advantageously made as high as possible while still maintaining desirable properties for processability, such as solubility in a solvent suitable for solution coating processes which are within the skill in the art, or melt processability such as extrusion, injection molding or melt blowing. In addition, the molar percent composition of the photoactive site is advantageously optimized to maintain the same features of processability. Optimization of molecular weight and molar composition of the photoactive site enhance the photochemical sensitivity as defined by Minsk et al. in The Journal of Applied Polymer Science, Volume 2, p. 302 (1959), or by Robertson et al. ibid, p. 308.

Similarly, in systems where the photoactive monomer has three or more trifluorovinyl groups, or is polymerized in a system containing a comonomer with three or more trifluorovinyl groups in sufficient quantity to result in a thermoset polymer, the molecular weight of the polymer (preferably prepolymer) is advantageously as close to the gel point of the system as possible while still maintaining processability as defined above, including solvent solubility and/or melt processability. In this case, processability also involves the exclusion of gels or very high molecular weight fractions which may form before the gel point, but which adversely affect the processability of the polymer and the quality of the coatings and laminates obtained from these prepolymers in applications where properties such as planarization and optical uniformity are important. In addition, the molar content of the photoactive site is optimized to provide maximum photochemical sensitivity as defined for the linear polymers. In general, weight average molecular weights on the order of 5,000 to 500,000, most preferably from about 10,000 to about 300,000 are useful in these systems.

When the polymer is a thermoplastic, however, it is advantageously applied in a liquid media as described but at a weight average molecular weight greater than about 20,000, preferably greater than about 60,000. Such high molecular weight polymers are advantageously applied in liquid media, preferably solutions such as by spin coating, spray coating, dip coating, pad printing and other methods known to those skilled in the art. Whereas a post application baking step is used for thermoset resins of the invention, thermoplastics are advantageously applied in a sufficiently high molecular weight to obviate the need for a post bake step. Alternatively, thermoplastic polymers of the invention are applied in melted form such as in a melt extruder, by melt coextrusion of a multilayer laminate, or by spin coating, dip coating or spray coating the polymer directly from the melt phase. The polymer may also be formed into a free standing film by melt extrusion, blow molding or other means known to those skilled in the art.

Alternatively, the polymer is applied as a dry film as is within the skill in the art for instance as discussed in Printed Circuits Handbook, C. F. Combs, Jr., ed., second ed., McGraw-Hill, New York, 1979, pages 6–12 through 6–13. In a dry film application, a film of photoactive polymer is advantageously supplied as a layer on one, or preferably between two, polymer sheets. The film is advantageously applied to a material such as a conductor, for example copper, is exposed to light such that the viscosity of the exposed photoactive polymer increases leaving the unexposed polymer unchanged for removal.

Photoactive polymers prepared by any of the foregoing methods are advantageously used as coatings. For use as coating, the polymer is preferably prepared in an organic solvent, aqueous medium, emulsion, or latex or is dissolved or dispersed after formation or used as a dry film. The coating is applied to a surface by means within the state of the art, such as by spin coating, spray coating, plasma deposition, roll coating, pad printing, dip coating and the like. Then the polymer is exposed or at least a portion of the polymer is selectively exposed to photonic radiation of a wavelength which interacts directly or indirectly with the photoactive sites. Preferably, sufficient photonic radiation is used to render the polymer less soluble or dispersible, more preferably essentially insoluble or not dispersible (that is insufficiently soluble or dispersible to be removed from the surface by rinsing in the solvent used for application or any other solvent(s) effective for removal of the unexposed portion of the polymer) or more viscous.

The polymer is suitably applied to any surface such as the surface of flat, spherical, irregular shapes, such as glass plates, silicon or silicon oxide wafers such as those used in the production of semiconductor devices, glass beads, copper film, other polymers including for instance polycarbonate, polyimide, polyester, polytetrafluoroethylene or other fluoropolymers, polyquinolines, polybenzoazoles, polybenzimidazoles, polyaryl sulfones , microelectronic circuitry including multilayer microelectronic circuitry devices or other surfaces of the like which optionally may be prepared by processes such as cleaning by washing with soap followed by rinsing with deionized water and then drying, either in an oven or with a stream of dry gas such as airy or cleaning by a plasma cleaning process such as oxygen plasma or sulfur hexafluoride plasma cleaning. Other surface treatments may include preparing the surface with an adhesion promoter such as bis[3-(triethoxysilyl)propyl] amine using standard conditions such as those outlined in "Silicon Compounds-Register and Review," published by Petrarch Systems Silanes and Silicones (1987), Petrarch Systems.

Any incident photonic radiation which is effective to render the polymer less soluble or dispersible (hereinafter effective wavelength) is suitably used. Such radiation is advantageously at a wavelength which is absorbed by the photoactive site, preferably from about 250 nm to about 500 nm, for instance 405–436 nm for sites having the 4-dimethylaminochalcone group, 300–365 nm for sites having the 4-methoxychalcone group, 254–280 nm for sites having the α-methylstilbene group, 300–365 nm for sites having the (unsubstituted) chalcone group, 300–365 nm for sites having the 1,4-pentadiene-3-one group, and the like. Alternatively, another compound can absorb the photonic radiation and change the available energy. For instance, compounds referred to as photosensitizers, such as benzophenone, 1,2-benzanthraquinone, or Michler's ketone are known in the art to absorb light at a wavelength different from the absorption of the photoactive site, and transfer the absorbed energy via collision processes from the photosensitizer to the photoactive site, activating the photoactive site for covalent reaction with an appropriate site for crosslinking. Thus, the photonic energy is suitably used directly or indirectly.

While the photosensitizer compounds are effective to increase the effective wavelength to those more commonly used in industry, use of wavelengths in the mid and deep ultraviolet (UV), that is wavelengths such as the 313 nm (nanometer) line for mid UV, and the 254 nm line for deep UV are advantageous especially for formation of coatings having very fine definition because resolution is improved. Most commonly used photoimageable polymers are active in the near UV region rather than the more desirable mid and deep UV. In a preferred embodiment of this invention, the photoactive group is active with a wavelength of incident photonic radiation of from about 235 to about 260 or from about 250 to about 275 to avoid optical density from the presence of aromatic groups.

Advantageously, to reduce solubility or dispersibility, the photoactive group acts such that crosslinking occurs as a result of incident photonic energy. Crosslinking optionally occurs between like photoactive groups or between a photoactive group and a group which is not photoactive. Most photoactive compounds of the invention react to crosslink through chemical reactions at the photoactive site, and generally involve lower energy (longer wavelength, e.g. >320 nm) absorptions of molecules with large and diffuse molecular orbitals, usually spread out over one or more aromatic ring systems. A benzophenone chromophore reacts somewhat differently however, irradiation of benzophenone with light excites the benzophenone carbonyl group to the excited singlet state, which crosses to the chemically active triplet state. During this excitation of the carbonyl group, the II bond is broken and the triplet state can be considered as a 1,2 diradical, which is believed to abstract hydrogen from hydrogen-donor molecules such as hydrocarbons, alcohols, ethers, amines, thiols, sulphides, and phenols and produce a benzophenone ketyl radical, also called a diphenylhydroxymethyl radical or semipinacal radical which radical reacts with another part of the polymer such that crosslinking occurs.

In the practice of the invention, it is preferred that crosslinking occurs such that the resulting group is not photoactive or photoabsorptive at the effective wavelength, preferably not photoactive at any wavelength. When photoactive groups continue to absorb photonic radiation at substantially the same wavelength (a wavelength sufficiently close to the effective wavelength to absorb at least a portion of the incident photonic radiation)after solubility or dispersibility is reducer they prevent that photonic radiation from going deeper into the polymer to cause another photoactive group to react. A material having groups which absorb photonic radiation at a given wavelength are referred to as having optical density at that wavelength. At reduced optical density, there is transparency that permits the photonic radiation to go deeper within a polymer. The deeper penetration of photonic radiation permits curing of thicker films or layers of polymer than is possible in a polymer with a higher optical density. Thus, practice of this preferred embodiment of the invention permits formation of thicker films than is possible in systems where optical density remains after solubility or dispersibility is reduced. For instance films having a high optical density are generally limited to a thickness of less than about 10 μm, but films of greater than about 2 μm preferably greater than about 5 μm more preferably greater than about 10 μm are formed in the practice of the invention. Films of the invention are advantageously at least about 0.01 μm, preferably at least about 0.1 μm, more preferably at least about 0.5 μm thick. Formation of such thick films also is facilitated by the lack of volatiles (water or molecules eliminated in formation of the final polymer film) formed in the practice of the invention.

Photoactive groups that result in crosslinking not having optical density at the effective wavelength include chalcones; cinnamates; acrylates; cinnamaldehydes; maleimides; 1,5-aryl-1,4-pentadiene-3-ones naphthoquinones; coumarins; (benzylidene) cyclohexanones; 2,6-bis(benzylidene)cyclohexanones; 2-cinnamylidene cyclohexanones; 1,9-bis(aryl)- 1,3,6,9-nonatetraene-5-ones; 2,6-bis(cinnamylidene)cyclohexanones; and stilbenes.

For use as a negative photoresist, only a portion of the photoactive polymer is exposed to sufficient photonic radiation to render it less soluble or dispersible. The remaining portion is referred to as unexposed and is removed by means within the skill in the art such as by a process known as developing, such as by spray development, which includes steps of spraying a film-coated substrate with a continuous stream of atomized or otherwise dispersed stream of a developing solvent for a sufficient time to efficiently remove the uncrosslinked portion of a polymer, followed by a drying step comprised of for instance either oven drying the substrate, or drying with a continuous stream of dry gas such as air or nitrogen, or a combination of both oven-drying and gas drying. Alternative means of removing the less soluble portion of polymer include dunk rinsing, which involves immersing the substrate in a bath of the developing solvent for sufficient time to dissolve the uncrosslinked portion of the polymer.

When the polymer has remaining trifluorovinyl groups, such as in the case of oligomers or B-staged polymers, the polymer is advantageously heated sufficiently to allow at least a portion of the trifluorovinyl groups to form perfluorocyclobutane groups, advantageously further building molecular weight of the polymer such that it becomes less soluble, more oxidatively and thermally stable, less swellable by contact with solvent, and attains a low dielectric constant and a dissipation factor which is characteristic of the perfluorocyclobutane ring containing polymers. Temperatures and conditions for forming perfluorocyclobutane groups are those disclosed in the previously cited patents.

Such coatings are also advantageously optically transparent and may be suitable as scratch resistant or chemically resistant coatings on optical lenses or other devices where optical transparency is an important feature.

Polymers formed in the practice of the invention advantageously have low moisture absorption, preferably moisture absorption of less than about 2 percent, low dielectric constant, preferably below about 3.5, low dissipation factor, preferably below about 0.01, flame retardency, good mechanical properties such as tensile modulus and flexural modulus of at least about 150,000 psi (about 1,034,213 kPa) chemical resistance, such as resistance to hydrocarbon, aromatic ring-containing solvents including benzene, chlorobenzene, nitrobenzene, toluene, xylene, mesitylene, and the like, ketone or halocarbon solvents, and high thermal-oxidative stability, preferably above about 100° C., preferably 150° C., more preferably 200° C., (advantageously formulated without added antioxidant). Polymers with at least some of these properties are particularly useful in fabrication of dielectric polymer films for microelectronics applications.

The following examples are offered to illustrate but not limit the invention. Examples (Ex.) of the invention are designated numerically, while Comparative Samples (CS) are not examples of the invention and are designated alphabetically. All parts, ratios, percentages and fractions are by weight unless designated otherwise.

EXAMPLE 1

Synthesis and Polymerization of
4,4'-Bis(trifluoroethenyloxy)-α-methylstilbene 4,4'-Bis(2-bromotetrafluoroethoxy)-α-methylstilbene:

4,4'-bis(hydroxy)-α-methylstilbene (100.0 g, 0.442 mole) is added to a 3 liter, 4 necked round bottomed flask along with DMSO (dimethylsulfoxide) (1150 ml) and toluene (350 ml). The resulting mixture is deoxygenated with nitrogen for 15 minutes, then KOH (58.4 g, 0.884 mole as 85 percent pellets, the remaining 15 percent being water) is added all at once. The mixture is stirred and heated to reflux, and water is removed azeotropically by distillation of the water/toluene azeotrope for a total of 10 hours. A Soxhlet extractor containing a drying bed of anhydrous $Na_2SO_4$ is placed on the reactor, and the toluene is refluxed through this drying bed to remove residual water. Toluene (260 ml) is removed by simple distillation, then the remaining mixture is cooled to 24° C. 1,2-Dibromotetrafluoroethane (276 g, 1.06 mole) is added slowly over 30 minutes, and the reaction mixture is stirred at 24° C. for 8 hours. After filtration and evaporation, the residue is flushed through a column of alumina using hexane as the eluent. Hexane is removed by evaporation, and the resulting residue weighs 109.4 g (0.19 mole) for an isolated yield of 42 percent.

Mass Spectrometric Analysis: m/e(mass/charge ratio)= 165 (9.6 percent); 179 (9.5 percent); 387 (10.0 percent); 389 (10.0 percent); 582 (41.1 percent); 583 (21.5 percent); 584 (100 percent); 585 (20.6 percent); 586 (47.1 percent)

4,4'-Bis(trifluoroethenyloxy)-α-methylstilbene:

The intermediate product 4,4-bis( 2-bromotetrafluoroethoxy)-α-methylstilbene (106.43 g, 0.18 mole) is added to 100 ml of acetonitrile in a 250 ml dropping addition funnel attached to a 1 liter 5-necked round bottomed flask. Zinc granules (40 mesh, 25.0 g, 0.38 mole) are added to the reactor along with 100 ml of acetonitrile, and the resulting stirred suspension is deoxygenated with nitrogen for 10 minutes by introducing nitrogen gas through a gas dispersion tube. The suspension is then heated to 75° C., at which point the addition of intermediate product solution in acetonitrile is begun. The addition is carried out over 20 minutes, and the resulting mixture is heated at 75° C. overnight. After centrifugation to remove suspended solids, the resulting supernatant is evaporated to dryness, leaving a crude product which is filtered through a short bed (4 cm) of alumina in a 600 ml sintered glass filter funnel using hexane as the eluent. After removal of the hexane by evaporation, the product is heated at 55° C. under high vacuum for 30 minutes.

Mass Spectrometric Analysis: m/e=191 (20.7 percent); 192 (12.2 percent); 386 (100 percent); 387 (22.2 percent).

α-Methylstilbene Perfluorocyclobutyl Ether Polymer:

A small sample (2.0 g) of the 4,4'-bis(trifluoroethenyloxy)-α-methyl-stilbene monomer is placed in a 50 ml 3-necked round bottomed flask fitted with a mechanical stirrer and a temperature controller. The monomer is agitated slowly as nitrogen is bubbled through the liquid for 5 minutes. The temperature of the flask is raised to 160° C. for 90 minutes, then to 180° C. for 60 minutes, and finally to 200° C. for 90 minutes. After it is cooled to room temperature, the resulting polymer is recovered by breaking pieces of the polymer out of the reaction flask, and a small portion of the polymer is dissolved in benzene. The benzene solution is filtered to remove any insoluble portion of the polymer and deposited on a salt plate for infrared (IR) analysis. The benzene is evaporated at 130° C. in an oven to leave a thin polymer film deposited on the salt plate.

Examination of the IR spectrum of the polymer reveals a medium absorption at 837 $cm^{-1}$, indicative of a carbon-hydrogen stretch associated with the hydrogen attached to a carbon-carbon olefin bond between two aromatic rings in the a-methylstilbene structure. The salt plate is then placed under UV irradiation at 254 nm for 3 hours. Analysis of the UV-cured film by IR indicates a significant decrease in the carbon-hydrogen absorption at 837 $cm^{-1}$. This loss of intensity at 837 $cm^{-1}$ is attributed to the disappearance of the carboncarbon double bond between the aromatic rings of the α-methylstilbene as this structure dimerizes upon irradiation with UV light at 254 nm. Subsequent irradiation overnight with light of 254 nm wavelength produces little change in the spectrum as compared to irradiation for 3 hours.

The resulting polymer film deposited on the salt plate is washed extensively with benzene in an effort to dissolve and thereby remove the polymer film which had originally been deposited from benzene solution. After being washed in 50 ml of benzene for 5 minutes, the salt plate is removed and the benzene allowed to evaporate to dryness. The IR spectrum of the salt plate is taken again, and no measurable loss of absorption intensity of the polymer film is observed with respect to the film before washing with benzene. This demonstrates that the polymer film is substantially intact after being washed with the solvent originally used to deposit the soluble form of the polymer, and indicates a degree of crosslinking in the polymer sufficient to render it insoluble in a solvent in which it is soluble prior to irradiation with UV light at 254 nm.

EXAMPLE 2

Copolymerization of 20 Mole Percent 4,4'-Bis(trifluoroethenyloxy)-α-methylstilbene with 80 mole Percent 1,1,1-Tris(4-trifluoroethenyloxyphenyl)ethane (TVE Monomer) and Subsequent Photocrosslinking of the Copolymer A mixture of 4,4'-bis(trifluoroethenyloxy)-α-methylstilbene (1.01 g, 0.0026 mole) and 1,1,1-Tris( 4-trifluoroethenyloxyphenyl)ethane (prepared here and in all examples as described in U.S. Pat. No. 5,066,746. (5.66 g, 0.010 mole) is placed in a 100 ml round bottomed flask equipped with a mechanical stirrer and and deoxygenated by introducing nitrogen into the flask through a gas dispersion tube for 10 minutes. The resulting mixture is then heated to 150° C. with stirring for one hour. The resulting prepolymer is cooled to room temperature, and a 1.0 g sample of the prepolymer is removed from the flask. This sample is combined with 10 ml of benzene in a 100 ml Erhlenmeyer flask and heated to 45° C. with stirring for 1 hour. The resulting polymer solution is deposited on a NaCl salt plate and the benzene solvent is evaporated to dryness in a drying oven at 120° C. Infrared (IR) analysis of this salt plate shows an absorption spectrum of the copolymer, with characteristic IR absorptions at 1605 $cm^{-1}$, 1594 $cm^{-1}$, and 1505 $cm^{-1}$, corresponding to the aromatic ring absorptions of the polymer system, and at 1206 $cm^{-1}$, 1175 $cm^{-1}$, and 1141$cm^{-1}$, corresponding to the absorption of the carbon-fluorine bonds. After irradiation of the film with UV light at 254 nm wavelength for 64 hours, a broad absorption band of moderate intensity from 1685 $cm^{-1}$ to 1772 $cm^{-1}$ appears. The salt plate is immersed in benzene and washed by swirling the benzene solvent over the salt plate for two minutes. Subsequent IR analysis of the washed plate reveals no decrease in the absorbance intensity, indicating that the polymer film is still substantially intact. This example demonstrates that the polymer is rendered insoluble to a solvent in which it is soluble before irradiation by irradiation with UV light at 254 nm wavelength.

EXAMPLE 3

Synthesis of 1,5-Bis( 4-trifluoroethenyloxyphenyl)-1,4-pentadiene-3-one 4-(2-bromotetrafluoroethoxy)benzaldehyde:
Method 1:
Dimethylsulfoxide (210 ml) and toluene (75 ml) are placed in a 500 ml 5-necked round bottomed flask equipped with a mechanical stirrer, a Barrett trap topped with a nitrogen padded reflux condenser, and a thermocouple attached to a temperature controller which controls a heating mantle on the flask through a Variac rheostat power supply. The solution is deoxygenated by bubbling nitrogen into the reactor for 10 minutes. Potassium hydroxide (KOH) (23.0 g, 0.35 mole as 85.5 percent pellets, the remainder is water) is added to the solution and the mixture is heated to 110° C. to dissolve the KOH. 4-Hydroxybenzaldehyde (42.7 g) is added in two equal portions. The solution is heated to reflux to begin water removal. When 14 ml of lower phase has been collected in the Barrett trap, the trap is replaced with a Soxhlet extractor containing anhydrous $Na_2SO_4$ (sodium sulfate), and the residual water in the toluene is removed by distilling the toluene through this $Na_2SO_4$ drying bed. Toluene (50 ml) is removed by simple distillation, and the resulting mixture is cooled to 60° C. 1,2-Dibromotetrafluoroethane (140 g, 0.538 moles) is added slowly and the mixture is heated to 70° C. After 2.5 hours of heating at 70° C., the mixture is heated to 85° C. overnight. The resulting reaction mixture is cooled, filtered and extracted with hexane (4 times, 400 ml each). The hexane extracts are combined and washed with distilled water (6 times, 500 ml each). After evaporation of the hexane a yellow oil remains, which is flash distilled on a Kugelrohr apparatus (80°–90° C., 0.20 mm Hg (26.6 Pa)) to provide a colorless liquid (8.35 g, 0.028 mole) in 7.9 percent yield.
Method 2:
Powdered 4-hydroxybenzaldehyde (351.4 g, 2.584 mole) is added slowly to a stirred solution of KOH (169.5 g, 2.584 mole as 85.5 percent pellets also containing 15 percent water) in 1600 ml of methanol which has been thoroughly deoxygenated by introducing nitrogen through a gas dispersion tube for a period of 15 minutes. The mixture is stirred for 1 hour under a nitrogen atmosphere, then evaporated to yield a purple solid. This solid product is placed in a vacuum drying oven at 5 mm Hg (665 Pa) and 110° C. for 5 hours, then removed, ground into a fine powder and placed in the. vacuum drying oven at 5 mm Hg (665 Pa) and 110° C. overnight. A total of 410.5 g (2.56 mole, 99.3 percent yield) of the potassium salt of p-hydroxybenzaldehyde is isolated by this method.

A portion of this salt (208.0 g, 1.3 mole) is added to 1200 ml of DMSO in a 3-liter round bottomed flask fitted with a vacuum sealed mechanical stirrer, a thermocouple well, a gas inlet valve and a Soxhlet extractor and condenser unit which is connected to a vacuum pump. An oven dried ceramic thimble in the Soxhlet extractor contained activated 5 A molecular sieves. The mixture is stirred slowly under high vacuum and heated to distill the DMSO through the Soxhlet drying apparatus. This distillation is continued until the DMSO solution measures 500 ppm $H_2O$ by Karl-Fisher titration.

After the system is vented to ambient pressure under dry nitrogen and the reaction mixture is cooled to 45° C. 1,2-dibromotetrafluoroethane (390 g, 1.50 mole) is slowly added to the reaction mixture through a dropping addition funnel. A temperature of 45° C. is maintained throughout the addition, and thereafter for 1hour. The temperature is then raised to 50° C. for 30 minutes, then to 55° C. for 20 minutes, then to 65° C. for 1 hour, and finally to 75° C. overnight. After being cooled to room temperature, the resulting crude reaction mixture is extracted with hexane (6 times with 1 liter portions). The hexane extracts are combined and evaporated to leave a portion of the product as a yellow oil. The remainder of the product is codistilled from the crude reaction mixture with the DMSO solvent. This DMSO/product mixture (1 liter) is diluted with 1200 ml of water and extracted again with hexane (4 times with 1 liter portions). These hexane extracts are combined with the yellow oil from the first extraction and washed with 250 ml of distilled water. After evaporation of the hexane layer, a light yellow oil remains. This oil is flash evaporated on a rotary evaporator (75° C., 0.5 mm Hg (66.5 Pa)) to provide a water white oil (136.07 g, 0.452 mole, 34.8 percent yield), 98.6 percent pure by gas chromatography (GC) analysis.

Mass Spectrometric Analysis: m/e=299 (58 percent); 300 (33 percent); 301 (100 percent); 302 (13 percent); 303 (31 percent).

4-Trifluoroethenyloxybenzaldehyde:

Acetonitrile (300 ml) and granular zinc (30.0 g) are combined in a 1 liter round bottomed flask and stirred at 75° C. under nitrogen as 4-(2-bromotetrafluoroethoxy)benzaldehyde (111.39 g, 0.37 mole) is added slowly by dropping addition funnel. The resulting mixture is stirred and heated at 79° C. for 12 hours. After filtration to remove zinc salts and unreacted zinc, the acetonitrile is removed under vacuum on a rotary evaporator. The resulting oily residue is flash distilled on a rotary evaporator under high vacuum (26.6 Pa) to provide 47.33 g (0.234 mole) of a water white oil in 63.3 percent yield.

Mass Spectrometric Analysis: m/e=51 (56 percent); 77 (65 percent); 105 (31 percent); 127 (37 percent); 154 (21 percent); 201 (34 percent); 202 (100 percent); 203 (70 percent).

Alternatively the compound is prepared from methyl-4-hydroxy-benzoic acid, salts or esters thereof or from phenol.

1,5-Bis(4-trifluoroethenyloxyphenyl)-1,4-pentadiene-3-one:
Method 1:

Acetone (0.70 g, 0.012 mole) and 4-trifluoroethenyloxybenzaldehyde (5.0 g, 0.0247 mole) are combined in reagent alcohol (90 percent ethanol, 5 percent methanol, and 5 percent isopropyl alcohol, available from Fisher Scientific) (30 ml) in a 250 ml jacketed 3-necked round bottom flask equipped with a mechanical stirrer, a nitrogen padded reflux condenser with a downstream gas flow indicator (a bubbler) and an inlet gas dispersion tube. The solution is cooled to 0° C. with stirring by circulating chilled glycol through the jacket of the reaction vessel, and is deoxygenated by introducing nitrogen through a gas dispersion tube into the solution for 15 minutes. A temperature of 0°–5° C. is maintained as the nitrogen gas flow is ceased and the alcohol solution is saturated with HCl (hydrochloric acid) by introducing gaseous anhydrous HCl through the gas inlet tube. The solution is stirred at 5° C. for 5 hours, then filtered, and the precipitate washed with 20 ml of fresh alcohol. The white crystalline product thus obtained (1.4 g, 0.0032 mole, 27.4 percent yield) has a melting point of 113°–114.5° C.

Mass Spectrometric Analysis: m/e=76 (16 percent); 102 (33 percent); 203 (13 percent); 329 (11 percent); 426 (100 percent); 427 (24 percent).

Method 2:

Reagent alcohol (110 ml) and 4-trifluoroethenyloxybenzaldehyde (20.0 g, 0.099 mole) are combined in the apparatus of Method 1 (with the addition of a septum on one neck of the apparatus, through which is introduced the needle of a syringe containing the reagent acetone), deoxygenated as in Method 1 and cooled to 0° C. with stirring. The temperature is maintained at 0°–5° C. as the alcohol solution is saturated with anhydrous HCl as in Method 1. When the alcohol solution has reached saturation, as is indicated by excess HCl exiting the reaction flask through the downstream gas flow indicator, the addition of acetone (2.87 g, 0.0495 mole) is begun. The acetone is added in small portions (0.50 ml each) at 30 minute intervals, for a total addition time of 3.5 hours. The continuous feed of anhydrous HCl gas is allowed to continue overnight at a slow pace (10 ml per minute). The HCl feed is then stopped and nitrogen gas is bubbled through the solution for 1 hour to remove some of the dissolved HCl. The reaction mixture is then filtered, and the precipitate is washed twice with deionized water (50 ml each). The precipitate is air dried for 20 minutes to provide 10.46 g (0.0245 mole) of the desired product. The filtrate is evaporated to a red oil, which is dissolved in acetonitrile (70 ml) and extracted with two portions of hexane (600 ml each). The extracts are combined and evaporated to provide an additional 0.55 g of the product, for a total of 11.01 g (0.0258 mole, 52.2 percent yield) as a light pink crystalline solid with a melting point of 111°–113° C.

EXAMPLE 4

Preparation and Photocrosslinking of a Copolymer
of 1,5-Bis(4-trifluoroethenyloxyphenyl)-
1,4-pentadiene-3-one and
4,4'-Bis(trifluoroethenyloxy)biphenyl A sample of the monomer 4,4'-bis(trifluoroethenyloxy)biphenyl, prepared as described in U.S. Pat. No. 5,023,380 (1.42 g, 0.0041 mole) is combined with the monomer 1,5-bis(4-trifluoroethenyloxyphenyl)-1,4-pentadiene-3-one (0.58 g, 0.00136 mole) in a 100 ml 3 necked round bottomed flask fitted with a mechanical stirrer, a temperature controller and a nitrogen inlet. The reactor is swept with nitrogen as the mixture of monomers is heated to 155° C. The temperature is controlled at 155° C. for 2 hours; then the heat is removed. A portion of the resulting yellow prepolymer is removed, dissolved in dichloromethane ($CH_2Cl_2$) and deposited between two NaCl salt plates for IR analysis. The two salt plates are rubbed together with the solution of prepolymer between them, then separated. The solvent is allowed to evaporate from each plate, leaving roughly identical films of prepolymer on each of the two plates.

One plate is placed in a plastic bag and stored in the dark as a control for the experiment. The second plate is placed in a round bottomed flask, and the flask is deoxygenated carefully with nitrogen. This plate is then subjected to irradiation with a 15 watt GE F15T8/BLB blacklight (360 nm) for 90 minutes. The two salt plates are then analyzed by IR spectroscopy. The first salt plate (experimental control) exhibits a complex absorption structure in the region normally associated with carbon-carbon double bonds, with small to medium absorptions at 1674 $cm^{-1}$, 1657 $cm^{-1}$, 1623 $cm^{-1}$, 1604 $cm^{-1}$, and 1585 $cm^{-1}$. By contrast, the IR spectrum of the plate which had been subjected to irradiation at 360 nm showed only a single absorption band in this region at 1606 $cm^{-1}$, all other absorptions in this region becoming minimal. This indicates that irradiation of the polymer film on the second salt plate has effected a change in the absorbance of the carbon-carbon double bond region of the IR spectrum by causing a light-induced intermolecular dimerization of some of the pentadienone carbon-carbon double bonds.

The second salt plate is then placed back in the round bottomed flask and irradiated with the blacklight for an additional 16 hours, while the first plate is returned to dark storage for the same period of time. Subsequent IR analysis of the two plates shows no noticeable differences from the spectra taken previously, after the second plate has experienced only 90 minutes of irradiation at 360 nm.

The two salt plates are then simultaneously placed in a 250 ml evaporating dish containing 50 ml of $CH_2Cl_2$, just enough to completely immerse the plates. The evaporating dish is then swirled gently for 1 minute to wash the solvent back and forth across the surfaces of the salt plates. The two plates are then removed and analyzed again by IR spectroscopy. The first plate, which has been stored in the dark, shows no absorption spectrum at all, indicating that the polymer film which is deposited there has been completely washed away by the $CH_2Cl_2$ treatment. The second salt plate, which has been subjected to irradiation with light at 360 nm, showed no decrease in the absorption spectrum after the $CH_2Cl_2$ treatment, indicating that the irradiated film is still substantially intact. This example demonstrates that a polymer film which has been subjected to photonic radiation is rendered insoluble in a solvent in which it is initially soluble.

EXAMPLE 5

Synthesis of β-(4-trifluoroethenyloxybenzylidene)-4-trifluoroethenyloxyacetophenone Method 1:
4-(2-Bromotetrafluoroethoxy)acetophenone 4-Hydroxyacetophenone (351.4 g, 2.584 mole) is added slowly to a solution of KOH(169.5 g, 2.584 mole as 85.5 percent pellets (remainder water)) in 1600 ml of methanol which had been thoroughly deoxygenated by bubbling nitrogen through a gas dispersion tube. The solution is stirred for 1.5 hours, then evaporated to a wet powder. This powder is dried overnight in a vacuum drying oven at 115° C., removing once after 2 hours to grind it to a fine powder with a mortar and pestle. The powder is cooled to room temperature under vacuum in the oven. A total of 448.2 g (2.576 mole, 99.7 percent yield) is recovered as a pink/orange solid.

A portion of this solid (228.2 g, 1.31 mole) is added to 1250 ml of DMSO in a 3-liter round bottomed flask equipped with a vacuum-sealed mechanical stirrer, a thermocouple in a glass thermocouple well, a gas dispersion tube, and a Soxhlet extractor topped with a reflux condenser. A ceramic thimble in the Soxhlet extractor is filled with activated 5 A molecular sieves. After the mixture is thoroughly deoxygenated by introducing nitrogen through the gas dispersion tube for 15 minutes, the tube is removed and replaced by a glass stopper. The mixture is stirred slowly under high vacuum (266 Pa) and heated to distill the DMSO through the Soxhlet drying apparatus for 4 hours. The solution is vented to atmospheric pressure under nitrogen and cooled to room temperature. Analysis of the DMSO solution indicates a water content of 420 ppm (parts per million by weight) by Karl Fisher titration. The reaction mixture is chilled to 18° C. in an ice water bath, and addition of 1,2-dibromotetrafluoroethane (400.0 g, 1.54 mole) is carried out over 45 minutes. The mixture is held at 18° C. for 30 minutes, then allowed to warm to room temperature. Over the course of one hour the temperature is raised to 50° C. and is maintained at 50° C. for 18 hours. The temperature is then raised to 65° C. for 8 hours, after which the mixture is cooled to room temperature. The DMSO solvent is removed from the product at 85° C./2.0 mm Hg, (266 Pa) and the resulting dark residue is distilled on a Kugelrohr apparatus to provide 82.6 g (0.262 mole, 20.0 percent yield) of the 4-(2-bromotetrafluoroethoxy)-acetophenone.

Mass Spectrometric Analysis: m/e=299 (85.8 percent); 300 (30.1 percent); 301 (1 00 percent); 315 (19.9 percent), 317 (19.9 percent). Infrared spectral analysis ($cm^{-1}$): C=O (1690); Ar (1605, 1504); C-F (1203,1167,1132).
4-Trifluoroethenyloxyacetophenone 4-(2-Bromotetrafluoroethoxy)acetophenone (82.0 g, 0.406 mole) is combined with 175 ml of acetonitrile and placed in an addition funnel attached to a 500 ml round bottomed flask equipped with a reflux condenser, a mechanical stirrer, and a thermocouple attached to a temperature controller which controls a heating mantle on the flask through a Variac rheostat power supply. An additional 25 ml of acetonitrile is placed in the 500 ml flask along with granular zinc (32.0 g, 0.4895 mole). The resulting zinc slurry is stirred and heated to 78° C., at which point the addition of 4-( 2-bromotetrafluoroethoxy)acetophenone is begun. The addition is carried out over a period of 45 minutes, during which time the heat is increased to the reflux temperature of the mixture (82° C.). After the resulting mixture is stirred at reflux for 5 hours, analysis of the reaction mixture by gas chromatography indicates that all of the starting acetophenone product has been consumed.

The reaction mixture is then cooled to room temperature and decanted away from the unreacted zinc granules into water (400 ml) which has been acidified with 20 ml of 12N HCl. This aqueous mixture is extracted with dichloromethane (2 times, 250 ml each). This extract is evaporated to provide a yellow oil which is distilled on a rotary evaporator at 85° C. and 2 mm Hg (266 Pa). The resulting product is flushed through a short bed of neutral aluminum oxide using hexane as an eluent to provide 27.9 g (0.138 mole, 34 percent yield) of the 4-trifluoroethenyloxyacetophenone product as a water white oil.

Mass Spectrometric Analysis: m/e=76 (22.4 percent); 91 (41.0 percent); 104 (38.5 percent); 201 (100 percent); 216 (22.1 percent); 217 (12 percent).

Infrared Spectral Analysis ($cm^{-1}$): C=O (1689); Ar (1602, 1502); C-F (1203,1169,1144).

Alternatively, the compound is prepared from ethyl phenol or phenol.
β-(4-trifluoroethenyloxybenzylidene)- 4-trifluoroethenyloxyacetophenone Reagent alcohol (150 ml, Fisher Scientific) is combined in a 1 liter jacketed round bottomed flask with 4-trifluoroethenyloxyacetophenone (25.0 g, 0.116 mole) and 4-trifluoroethenyloxybenzaldehyde (23.4 g, 0.116 mole). The flask is equipped with a mechanical stirrer, a thermometer, and a gas dispersion tube. The mixture is stirred as chilled glycol coolant is circulated through the flask jacket to cool the mixture to 3°–5° C. Nitrogen gas is bubbled into the mixture through the gas dispersion tube to deoxygenate the solution. The inlet gas is then switched from nitrogen to anhydrous HCl and the feed rate is controlled to maintain a solution temperature of 5° C. This HCl feed is continued for 4.5 hours, at which point the HCl feed is stopped and the stirring is continued for an additional hour.

Cold water (250 ml) is then added slowly to the reactor. The resulting light yellow precipitate is filtered from the liquid, washed twice with 200 ml each of cold deionized water, then dissolved in 1000 ml of hot (60° C.) hexane. The resulting hexane layer is decanted away from the water layer and chilled in an ice bath to recrystallize the product. After filtration to remove the precipitate, the hexane filtrate is concentrated by evaporation on a rotary evaporator at 60° C. and chilled again to cause the crystallization of the product. Three batches of crystals are thus collected from the hexane phase and are combined to provide 26.9 g, (0.067 mole, 58.0 percent yield) of a fluffy white powder, melting point 93.5°–94.0° C.

Mass Spectrometric Analysis: m/e=102 (20.4 percent); 104 (17.1 percent); 178 (19.8 percent); 201 (17.2 percent); 206 (21.0 percent); 303 (37.3 percent); 399 (51.4 percent); 400 (100 percent); 401 (50.9% ).

Method 2:

β-(4-(2-bromotetrafluoroethoxy)benzylidene)-4-( 2-bromotetrafluoroethoxy)acetophenone A sample of 4-hydroxy-β-( 4-hydroxybenzylidene)acetophenone (4,4'-dihydroxychalcone, prepared according to the procedure of Zahir in Journal of Applied Polymer Science, volume 23, page 1355, (1979)) (229.0 g, 0.954 mole) is added to dimethylsulfoxide (DMSO) and toluene in a 2 liter 5-necked round bottom flask equipped with a mechanical stirrer, a Barrett trap topped with a nitrogen padded reflux condenser, and a thermocouple attached to a temperature controller which controls the power output to a heating mantle on the reaction vessel through a variable rheostat power source. The solution is deoxygenated by introducing nitrogen through a gas dispersion tube for 15 minutes. Potassium hydroxide pellets (125.4 g, 85 percent KOH by weight, the balance being water) are added to the solution and heating is begun. The nitrogen gas dispersion tube is removed and replaced with a glass stopper when the KOH pellets are completely dissolved, that is when the solution temperature reaches 110° C. The solution is heated to reflux (138° C.), and water is removed through the Barrett trap via azeotropic distillation with the toluene. A total of 99 ml of lower phase is removed from the Barrett trap over the course of 6 hours. The Barrett trap is then removed and replaced with a Soxhlet extractor containing activated 5A molecular sieves. The toluene is then distilled through the Soxhlet extractor drying bed for 3 hours. The Soxhlet extractor is then removed and replaced with the Barrett trap, and toluene (200 ml) is removed through the Barrett trap by simple distillation. The resulting solution is then cooled to 30° C., and the addition of 1,2-dibromotetrafluoroethane (600.0 g, 2.31 mole) is begun. The addition is carried out at 30°–35° C. over a period of 45 minutes. When the addition is complete, the mixture is heated slowly to 75° C. over 1 hour and stirred at 75° C. overnight.

After being cooled the mixture is added to a large excess of distilled water (4.0 L) and dichloromethane (500 mL) is added to the solution to facilitate phase separation. The dichloromethane phase is removed from the bottom and evaporated to provide crude product as a dark brown oil. The oil is dissolved in acetonitrile (1500mL) and placed in a continuous liquid/liquid extractor as the heavy source phase in an apparatus as described for continuous extraction for solvents lighter than water by F. Kutscher and H. Steudel in *Zeitschrift fur Physiologische Chemie*, volume 39, page 4747 (1903). The light phase which is continuously evaporated and recirculated is hexane. The extraction is run for 48 hours, and the hexane is evaporated. The residue remaining after evaporation is dissolved in toluene (300 ml) and flushed through a short bed of alumina. The toluene is evaporated, and a yellow crystalline product remains and is dissolved in a minimum amount of hot hexane (60° C.). The hexane is chilled in an ice bath to cause the crystallization of the product. After filtration to remove the precipitate, the hexane filtrate is concentrated by evaporation on a rotary evaporator at 60° C. and chilled again to cause the crystallization of the product. After filtration the precipitate fractions are combined to afford 208.6 g (0.35 mole, 36.6 percent yield) of the product β-(4-(2-bromotetrafluoroethoxy)benzylidene)- 4-(2-bromotetrafluoroethoxy)acetophenone as a light green solid with a melting point of 89°–90° C.

Mass Spectrometric Analysis: m/e=63 (16.9 percent); 92 (14.3 percent); 165 (15.8 percent); 299 (17.0 percent); 401 (55.0 percent); 402 (23.4 percent); 403 (60.5 percent); 404 (20.8 percent); 417 (12.7 percent); 419 (16.1 percent); 596 (62.3 percent); 597 (75.1 percent); 598 (100.0 percent); 599 (47.7 percent); 600 (47.6 percent).

β-(4-trifluoroethenyloxybenzylidene)- 4-trifluoroethenyloxyacetophenone

The product of the above reaction, β-(4-( 2-bromotetrafluoroethoxy)benzylidene)-4-(2-bromotetra-fluoroethoxy)acetophenone (5.0 g, 0.00836mole) is combined in a 200 ml 3-necked round bottom flask with 2-methoxy ethyl ether (20 ml) and granular zinc (4.37 g, 0.067 mole). The slurry is heated to 120° C. and stirred with a mechanical stirrer under a nitrogen atmosphere for 24 hours. The resulting reaction mixture is filtered and the filtrate is evaporated at 90° C. under reduced pressure (2.0 mm, 266 Pa) to remove the solvent. The residue remaining after evaporation is dissolved in acetonitrile (150 ml) and extracted with hexane (5 portions, 200 ml each). The hexane extracts are combined and evaporated at 60° C. and reduced pressure (20 mm, 2670 Pa) to a volume of 100 ml which is then allowed to cool to room temperature from 60° C. The product which crystallizes out of the hexane is collected by filtration and washed with cold hexane (25 ml, 5° C.). The hexane filtrates are combined and concentrated by evaporation at 60° C. and reduced pressure (20 mm, 2670 Pa) to a volume of 75 ml, then allowed to cool again to room temperature. A second batch of crystals is thereby collected after filtration of the hexane concentrate. The combined solids weigh 0.60 g (0.0015 mole, 17.9 percent yield) and have a melting point of 93.5°–94° C.

EXAMPLES 6–10

Preparation of Copolymers of
1,1,1-Tris(trifluoroethenyloxyphenyl)ethane with β-(
4-trifluoroethenyloxybenzylidene) -
4-trifluoroethenyloxyacetophenone, and a
Copolymer of 1,1,1-Tris
(trifluoroethenyloxyphenyl)ethane with 1,5-Bis(
4-trifluoroethenyloxyphenyl)-1,4-pentadiene-3-one For each of Examples 6–11, solid white 1,1,1-tris(trifluoroethenyloxyphenyl)ethane (TVE Monomer, 200 g) is added to a 500 mL one necked round bottom flask connected to a Kuglerohr apparatus and then deoxygenated at 80° C. under vacuum (0.20 mm Hg, 26.6 Pa) for 2 hours to give a colorless oil. The TVE monomer is then mixed with the stated amounts indicated in each example of β-(4-trifluoroethenyloxybenzylidene)- 4-trifluoroethenyloxyacetophenone (hereinafter chalcone monomer) prepared by the process of Example 5 or 1,5-Bis(4-trifluoroethenyloxyphenyl)-1,4-pentadiene-3-one (hereinafter bischalcone monomer) prepared by the process of Example 3 and B-staged according to the procedure outlined below.

EXAMPLE 6

5 Mole percent Chalcone/95 Mole percent TVE

TVE monomer (30 g) and chalcone monomer (1.18 g) are placed in a long cylindrical reaction vessel equipped with a three necked glass head, a Teflon™ (polytetrafluoroethylene commercially available from E. I. DuPont de Nemours and Co.) seal, a stirrer with a Teflon™ paddle, a screw clamp, a nitrogen inlet, and a vacuum outlet. The mixture is stirred at a constant speed, evacuated, vented two times with nitrogen, immersed in a fluidized aluminum oxide sand bath (preheated to 150° C.) to ⅔ its height and then heated at 150° C. with stirring for 3.50 hours under nitrogen. (Heating to achieve partial polymerization is referred to as B-staging.)

Upon cooling, the prepolymer is a yellow glass-like solid. After the temperature of the prepolymer reaches room temperature (22°–24° C.), the reactor is cooled with dry ice to facilitate removal of the prepolymer by cracking the embrittled prepolymer, thereby making it easier to remove from the reaction vessel. The prepolymer is ground to a fine powder with a mortar and pestle to give 28.45 g of a yellow solid. Analysis of the prepolymer by gel permeation chromatography (GPC) indicates a weight average molecular weight of 7,810 for this sample as standardized against polystyrene.

EXAMPLE 7

10 Mole percent Chalcone/90 Mole percent TVE.

TVE Monomer (30 g) and chalcone monomer (2.50 g) are combined and B-staged at 150° C. for 4 hours using the procedure of Example 6 to give 29.05 g of yellow solid prepolymer. Analysis of the prepolymer by GPC indicates a weight average molecular weight of 13,800 for this sample as standardized against polystyrene.

EXAMPLE 8

10 Mole Percent Chalcone/90 Mole Percent TVE.

TVE Monomer (30 g) and chalcone monomer (2.50 g) are combined and B-staged at 150° C. for 4.75 hours using the procedure of Example 6 to give 28.02 g of yellow solid prepolymer. Analysis of the prepolymer by GPC indicates a weight average molecular weight of 34,800 for this sample as standardized against polystyrene.

EXAMPLE 9

50 Mole percent Chalcone/50 Mole percent TVE.

TVE Monomer (30 g) and chalcone monomer (11.24 g) are combined and B-staged at 150° C. for 4.25 hours using the procedure of Example 6 to give 40.00 g of yellow solid prepolymer. Analysis of the prepolymer by GPC indicates a weight average molecular weight of 3,160 for this sample as standardized against polystyrene.

EXAMPLE 10

10 Mole percent Bischalcone/90 Mole percent TVE.

TVE Monomer (20 g) and bischalcone monomer (1.77 g) are combined and B-staged at 150° C. for 4 hours using the procedure of Example 6 to give 19.00 g of yellow solid prepolymer. Analysis of the prepolymer by GPC indicates a weight average molecular weight of 4,400 for this sample as standardized against polystyrene.

EXAMPLES 11–15

Spin coating a photosensitive prepolymer onto a 10-centimeter diameter silicon oxide wafer and photocrosslinking the prepolymer film In the following examples the silicon oxide wafers are pretreated with an adhesion promoter according to the following method:

Bis[3-(triethoxysilyl)propyl]amine (commercially available from Huls America Inc.) (0.50 g) is combined with distilled water (0.50 g) for 14 minutes to promote some prehydrolysis and condensation of the silane functionality. This solution is then diluted with 24 ml of methanol to form a 2 weight percent solution of the adhesion promoter in methanol. A portion of the adhesion promoter solution (5 ml) is drawn into a syringe and filtered through a 1.0 micron (0.001 mm) filter onto the surface of the silicon wafer which is spinning at 5000 revolutions per minute (rpm) on a Solitec Model 5100 Spin Coater. After the adhesion promoter is applied, the substrate continues to spin at 5000 rpm for 90 seconds to evaporate the water and methanol from the adhesion promoter coating.

EXAMPLE 11

Photocrosslinking of a Copolymer of 5 Mole Percent Chalcone Monomer/95 Mole Percent TVE Monomer The prepolymer of 5 mole percent chalcone/95 mole percent TVE monomer from Example 6 above (weight average molecular weight=7,810 g/mole) is dissolved to make a 50 percent solid solution in mesitylene. The prepolymer solution is filtered from a syringe through a 0.2 micron (0.002 mm) filter (to remove small particles) into a 100 mL clean bottle. The term 'clean bottle' is used to refer to a bottle which has been cleaned to contain less than 0.001 particle of size 0.30 micron or larger per milliliter of volume. The prepolymer solution (2 mL) is then deposited onto a 10 cm round silicon oxide wafer using a spread cycle of 500 rpm for 3 seconds and a spin cycle of 5000 rpm for 30 seconds to give a film of excellent quality (no large variation in film thickness as noted by the absence of unassisted visually detected colored interference patterns on the wafer). The prepolymer film is prebaked at 80° C. for 30 minutes to remove residual solvent and to enhance adhesion of the prepolymer onto the subtrate. The prepolymer film thickness as determined by an Alpha Step-200 Profilemeter is 1.572 microns.

The prebaked prepolymer (5 mole percent chalcone/95 mole percent TVE) is exposed to UV light (wavelength range=290–350 nanometers (nm), 1000 Watts) using a high pressure mercury xenon short arc lamp for an exposure time of 250, 500, 800, and 999 seconds (seconds.) using a fused silica quartz test mask for pattern transfer. The exposed film is then developed by soaking in xylene solvent for 15 seconds and then dried under a stream of nitrogen at a temperature of 25° C. A negative relief of the pattern on the quartz mask is sucessfully transferred to the polymer upon development as indicated by uncrosslinked areas within the pattern which are washed away by the developing solvent (xylene). The pattern results indicate that an exposure time of 999 seconds is sufficient to crosslink the prepolymer to an extent sufficient to render it insoluble in the developing solvent. Exposure times of 800 seconds or less under these conditions are found to be insufficient to pattern the film. Other solvents such as dichloromethane and 2-methoxyethyl ether are also excellent solvents for development under the same development conditions. The film thickness measured after UV exposure and development is determined to be 1.485 microns. The loss in film thickness is 6 percent after solvent development.

Following the general procedure of Example further examples of processing good quality thin films of photodefinable prepolymers onto 10 cm silicon oxide substrates are outlined in the following examples of the invention:

EXAMPLE 12

(10 mole percent chalcone/90 mole percent TVE)

B-Staging Conditions: 4.0 hours at 150° C.;
Spin Coating Conditions:
  Spread cycle: 500 rpm for 45 seconds.
  Spin cycle: 1500 rpm for 30 seconds to yield a 1.4 micron coating after photocrosslinking.
Polymer Prebake and Solvent Evaporation=80° C. for 30 minutes;
UV exposure time: 999 seconds
Developing solvent: 2-methoxyethyl ether for 15 seconds;
Thermal Cure: 2 hr (hour) ramp to 210° C. (hold 1 hr). ["2 hour ramp to 210° C." refers to raising the temperature from room temperature to 210° C. over a 2 hour period; then "hold 1 hr" means the plate is held at 210° C. for 1 hour.]

EXAMPLE 13

(10 mole percent chalcone/90 mole percent TVE)

B-Staging Conditions: 4.75 hours at 150° C.;
Spin Coating Conditions:
  Spread cycle: 500 rpm for 3 seconds.
  Spin cycle: 9000 rpm for 30 seconds to yield a 4.4
Polymer Prebake and Solvent Evaporation: 80° C. for 30 minutes;
UV exposure time: 999 seconds;
Developing solvent: 2-methoxyethyl ether for 15 seconds;
Thermal Cure: 2 hr ramp to 210° C. (hold 1 hr).

EXAMPLE 14

(10 mole percent chalcone/90 mole percent TVE)

B-Staging Conditions: 4.0 hours at 150° C.;
Spin Coating Conditions:
  Spread cycle: 500 rpm for 45 seconds.
  Spin cycle: 1500 rpm for 30 seconds to yield a 1.4 micron coating after photocrosslinking.
Polymer Prebake and Solvent Evaporation: 2 hours ramp from 50° C. to 120° C. (hold 1 hour);
UV exposure time: 999 seconds;
Developing solvent: 2-methoxyethyl ether for 15 seconds;
Thermal Cure: 2 hr ramp to 210° C. (hold 1 hr).

EXAMPLE 15

(10 mole percent chalcone/90 mole percent TVE)

B-Staging Conditions: 4.75 hours at 150° C.;
Spin Coating Conditions:
  Spread cycle: 500 rpm for 3 seconds.
  Spin cycle: 9000 rpm for 30 seconds to yield a 4.4 micron coating after photocrosslinking.
Polymer Prebake and Solvent Evaporation: 2 hours ramp from 50° C. to 120° C. (hold 1 hour);
UV exposure time: 999 seconds;
Developing solvent: 2-methoxyethyl ether for 15 seconds;
Thermal Cure: 2 hr ramp to 210° C. (hold 1 hr).

EXAMPLE 16

(50 mole percent chalcone/50 mole percent TVE )

B-Staging Conditions: 4.25 hours at 150° C.;
Spin Coating Conditions:
  Spread cycle: 500 rpm for 3 seconds.
  Spin cycle: 9000 rpm for 30 seconds to yield a coating of unknown thickness after photocrosslinking.
Polymer Prebake and Solvent Evaporation: 30 minutes ramp from 50° C. to 120° C. (hold 30 minutes);
UV exposure time: 999 seconds;
Developing solvent: 2-methoxyethyl ether for 15 seconds;
Thermal Cure: 2 hr ramp to 210° C. (hold 1 hr).

EXAMPLE 17

(10 mole percent bischalcone/90 mole percent TVE)

B-Staging Conditions: 4.00 hours at 150° C.;
Spin Coating Conditions:
  Spread cycle: 500 rpm for 3 seconds.
  Spin cycle: 9000 rpm for 30 seconds to yield a 1.0 micron coating after photocrosslinking.
Polymer Prebake and Solvent Evaporation: 2 hours ramp from 50° C. to 120° C. (hold 1 hour);
UV exposure time: 500 seconds;
Developing solvent: 2-methoxyethyl ether for 15 seconds;
Thermal Cure: 2 hr ramp to 210° C. (hold 1 hr). (See Table 1).

Conditions for photodefining the copolymer of the bischalcone (10 mole percent) with TVE (90 mole percent) in Example 17 are similar to those in the previous examplest except that the wavelength range of 350–450 nm used for pattern transfer (see Table 2). In an exposure time of 500 seconds, the energy dosage required for crosslinking 10 mole percent bischalcone/90 mole percent TVE prepolymer film of 4400 weight average molecular weight and 1.0 micron thickness is 30 J/cm$^2$ (at 365 nm).

TABLE 1

Photodefinable Conditions of Copolymer of Chalcone Monomer with TVE Monomer

| Example | Chalcone Monomer*/TVE mole percent/mol percent | B-Staging Time (hours) | Weight Average Molecular Weight | Prebake Conditions* | Dosage Time (seconds) | Quality** |
|---|---|---|---|---|---|---|
| 11 | 5/95 | 3.50 | 7,810 | 80° C. per 30 min. | 999 | F, D |
| 12 | 10/90 | 4.00 | 13,800 | 80° C. per 30 min. | 999 | F, D |

TABLE 1-continued

Photodefinable Conditions of Copolymer of Chalcone Monomer with TVE Monomer

| Example | Chalcone Monomer#/TVE mole percent/mol percent | B-Staging Time (hours) | Weight Average Molecular Weight | Prebake Conditions* | Dosage Time (seconds) | Quality** |
|---|---|---|---|---|---|---|
| 13 | 10/90 | 4.75 | 34,800 | 80° C. per 30 min. | 999 | F, D |
| 14 | 10/90 | 4.00 | 13,800 | 50° C. 2 hr. R 120° C. 1 hr. | 999 | E, ND |
| 15 | 10/90 | 4.75 | 34,800 | 50° C. 2 hr. R 120° C. 1 hr. | 999 | G, ND |
| 16 | 50/50 | 4.25 | 3,160 | 50° C. 30 min. R 120° C. 30 min. | 999 | G, NDT |

*R is "ramp to" that is increase the temperature from the first temperature over the period indicated before the "R" to the second temperature and hold it there for the final period.
**See explanation on next page
Chalcone monomer is β-(4-trifluoroethenyloxybenzylidene)-4-triflurorethenyloxyacetophenone.

In the last column, F, D=the quality of the wafer is fair and the polymer film delaminated during developement; E=excellent quality; ND=no delamination; NDT=no delamination on the top side of the wafer; however, some dissolving of the polymer closest to the silicon oxide wafer is observed. G=a good quality film was obtained. The difference between G and E is a subjective evaluation based on the surface appearance of the film, such as a good (G) quality coating appears smooth and uniform with a non-gloss or matte finish, and an excellent (E) quality film appears smooth and uniform with a glossy finish.

prepolymer film in the region of 260 nm to 450 nm); the spectra of the photoexposed prepolymer films has a decrease of absorbance at the position of the lambda max of the photocrosslinkable copolymer. The lambda max for the chalcone and bischalcone containing prepolymers are 314 and 330 nm, respectively.

The spectra and the optical density measurements for both photodefinable materials before and after UV exposure indicate that the copolymer "bleaches" (that is, it turns colorless from 260 nm to 500 nm) upon exposure to UV light. Data for the optical density measurements of the

TABLE 2

Photodefinable Conditions of Copolymer of Bischalcone Monomer with TVE

| Example | TVE mole percent/Bichalcone Monomer# mol percent | Weight Average Molecular Weight B-Stage Time (hours) | Prebake Conditions* | Dosage Time (seconds) | Quality** |
|---|---|---|---|---|---|
| 17 | 10/90 | 4,400 | 50° 2 hr. R 120° C. 1 hr. | 500 | G, ND |

*R is as in Table 1.
Bischalcone monomer is 1,5-Bis(4-trifluoroethenyloxyphenyl)-1,4-pentadiene-3-one.
**Quality is as for Table 1

EXAMPLES 18–20 and Comparative Sample A

Optical Density Measurements and Photobleaching of Photocrosslinkable Prepolymer Films Solutions of prepolymer (50 percent by weight) with the following compositions; 100 mole percent TVE (Comparative Sample A, not an example of the invention), 5 mole percent chalcone/95 mole percent TVE (Example 18), 10 mole percent chalcone/90 mole percent TVE (Example 19), 50 mole percent chalcone/50 mole percent TVE (Example 20) are each separately prepared in mesitylene. The solutions are filtered through a 0.20 micron filter and then spin coated on 10 centimeter quartz substrates using a spread cycle of 500 rpm for 3 seconds and a spin cycle of 9000 rpm for 30 seconds to yield the following film thicknesses before exposure to uv light; 1.042, 1.482, 1.398, 1.280, and 1.000 microns, respectively.

Each coated quartz wafer is exposed to UV light for 999 seconds between the wavelengths of 290–350 nm. The UV absorption spectra for each wafer is analyzed between 200 and 500 nm wavelengths with a Perkin Elmer Model Lambda 3B UV/VIS Spectophotometer before and after UV exposure. The spectra of the photocrosslinkable copolymer before photoexposure has the characteristic lambda max (that is the wavelength of maximum absorbance of the chalcone and bischalcone containing prepolymer films at 313 nm, 334 nm, and 365 nm before and after exposure to UV light appear in Tables 3 and 4, respectively.

These examples demonstrate bleaching of these photocrosslinkable copolymers after photoexposure.

TABLE 3

Optical Density for Copolymers of Chalcone Monomer with TVE Before Exposure to UV Light

| Example | Percent (Mol percent)* Chalcone Monomer in Copolymer | Optical Density at 313 nm | Optical Density at 334 nm | Optical Density at 365 nm |
|---|---|---|---|---|
| A** | 0 | 0.0000 | 0.0134 | 0.0081 |
| 18 | 5 | 0.2643 | 0.2007 | 0.0393 |
| 19 | 10 | 0.5676 | 0.3725 | 0.0472 |
| 20 | 50 | 3.7864 | 1.8289 | 0.3397 |

**Comparative sample not an example of the invention.
*Chalcone monomer is as in Table 1.

TABLE 4

Optical Density (OD) for Copolymers of Chalcone Monomer with TVE After Exposure to UV Light

| Example No. | Percent (Mol percent)* Chalcone Monomer in Copolymer | Optical Density at 365 nm | Optical Density at 313 nm | Optical Density at 334 nm |
|---|---|---|---|---|
| A** | 0 | 0.0000 | 0.0134 | 0.0081 |
| 18 | 5 | 0.0644 | 0.0664 | 0.0341 |
| 19 | 10 | 0.0870 | 0.0821 | 0.0433 |
| 20 | 50 | 0.3255 | 0.2140 | 0.1110 |

**Comparative Samples not an example of the invention.
*Chalcone monomer is as in Table 1.

EXAMPLE 21

Preparation of β-( 4-dimethylaminobenzylidene)-4-trifluoroethenyloxyacetophe none 4-Trifluoroethenyloxyacetophenone (prepared in Example 5 above, 10.0 g, 0.046 mole) is combined with dimethylaminobenzaldehyde (commercially available from Aldrich Chemical Co., 7.59 g, 0.051 mole) in 60 ml of reagent alcohol in the apparatus described for the preparation of β-(4-trifluoroethenyloxybenzylidene)- 4-trifluoroethenyloxyacetophenone in Example 5, Method 1, and stirred at 0°–5° C. with a slow feed of anhydrous HCl for 78 hours. Nitrogen is blown through the reaction mixture to remove some HCl, then the alcohol is evaporated to provide the crude product mixture. This mixture is dissolved in dichloromethane and carefully washed with aqueous potassium carbonate to neutralize the acid. The dichloromethane is evaporated, and the residue is subjected to column chromatography on alumina using hexane saturated with acetonitrile as an eluent, to provide 11.4 g (71 percent) of the β-( 4-dimethylaminophenyl)-4-trifluoroethenyloxyacetophenone as an orange crystalline solid with a melting point of 68°–72° C.

Spectral analysis of this product indicates a lambda max of 412 nm in acetonitrile solution, with an extinction coefficient of 29,560.

Mass Spectrometric Analysis: m/e=121 (7.4 percent); 146 (6.1 percent); 174 (6.1 percent); 250 (12.3 percent); 347 (10C percent); 348 (30.8 percent) is consistent with identification as β-(4-dimethylaminobenzylidene)- 4-trifluoroethenyloxyacetophenone.

EXAMPLE 22

Copolymerization of β-(4-dimethylaminobenzylidene)-4-trifluoroethenyloxyacetophenone and TVE monomer β-(4-dimethylaminobenzylidene)- 4-trifluoroethenyloxyacetophenone (1.4052 g, 0.00404 mole) prepared according to the procedure of Example 21 is combined with the TVE monomer (20.01 g, 0.0366 mole) and mesitylene solvent (21.4 g) in a 200 ml round bottomed flask equipped with a reflux condenser and a thermocouple attached to a temperature controller which controls a heating mantle on the flask through a Variac rheostat power supply. A magnetic stirring bar is placed in the flask, and the flask is placed on a magnetic stirrer to provide agitation during the polymerization process. The mixture is thoroughly deoxygenated by bubbling nitrogen through a gas dispersion tube into the stirred solution, and is thereafter maintained under a nitrogen atmosphere. The solution is heated to 160° C. with stirring for 5 hours, then cooled.

The molecular weight of the prepolymer is checked by gel permeation chromatography (GPC) as standardized against polystyrene. The weight average molecular weight is found to be 6,316. The solution is heated to 160° C. for an additional 65 minutes, after which time it is cooled and the molecular weight tested again. The weight average molecular weight of the prepolymer is 12,434 as determined by GPC as standardized against polystyrene. The solution is heated to 160° C. for an additional 60 minutes, then cooled to test the molecular weight. The weight average molecular weight of the prepolymer is 38,442.

EXAMPLE 23

Preparation of β-(4-methoxybenzylidene)-4-trifluoroethenyloxyacetophenone

4-Trifluoroethenyloxyacetophenone (10.0 g, 0.0463 mole) is combined with 4-anisaldehyde (commercially available from Aldrich Chemical Co.) (6.9 g, 0.050 mole) in reagent alcohol in the apparatus described for the preparation of β-( 4-trifluoroethenyloxybenzylidene)-4-trifluoroethenyloxyacetophenone in Example 5, Method 1 above, and is cooled to 0° C.–5° C. with stirring. After the solution is deoxygenated by bubbling nitrogen through a gas dispersion tube for 10 minutes, anhydrous HCl is introduced into the solution at a rate that maintains a solution temperature of 5° C. After 1.5 hours the solution turns red, and a solid precipitate begins to form. The HCl feed is stopped after 4 hours, and nitrogen is blown through the solution to remove some of the HCl. The alcohol is evaporated, and the remaining solid is dissolved in 100 ml of dichloromethane. The dichloromethane solution is carefully washed with aqueous potassium carbonate to neutralize the acid. The dichloromethane is then removed from the product by evaporation on a rotary evaporator. Analysis of the final product by gas chromatography indicates that the material is greater than 97 percent pure and requires no further purification.

This product has a melting point of 70.0°–71.5° C. Spectral analysis of this product indicates that it exhibits a lambda max of 338 nm in acetonitrile solution, with an extinction coefficient of 20,029.

Mass Spectrometric Analysis: m/e=89 (6.2 percent); 165 (8.6 percent); 303 (8.1 percent); 333 (9.8 percent); 334 (100 percent); 335 (51.3 percent); 336 (8.15 percent) is consistent with identification as β-( 4-methoxybenzylidene)-4-trifluoroethenyloxyacetophenone.

EXAMPLE 24

Copolymerization of β-( 4-methoxybenzylidene)-4-trifluoroethenyloxyacetophenone with TVE Monomer:

β-(4-methoxybenzylidene)- 4-trifluoroethenyloxyacetophenone (1.3544 g, 0.00405 mole) is combined with TVE monomer (20.02 g, 0.0366 mole) and mesitylene solvent (21.37 g) in the apparatus of Example 227 and is deoxygenated thoroughly by introducing nitrogen through a gas dispersion tube for 10 minutes, and thereafter maintaining the solution under a nitrogen atmosphere. The solution is heated to 160° C. for 3 hours and 10 minutes, after which time it is cooled and the solution is checked by GPC analysis to ascertain the molecular weight of the prepolymer. The weight average molecular weight of the prepolymer is 379,400.

What is claimed is:

1. A method of using a polymer having at least one photoactive site and plural perfluorocyclobutane groups as a coating comprising application of at least one such polymer, which polymer is at least partially soluble or dispersible, to a surface and exposing at least a portion of said polymer to incident photonic radiation sufficient to render the polymer so exposed less soluble or dispersible.

2. The method of claim 1 wherein a monomer having at least one photoactive site or photoactive precursor is used in an amount of at least about 0.1 percent by molar composition in the polymer.

3. The method of claim 2 wherein at least about 1 mole percent of the monomer is used.

4. The method of claim 3 wherein from about to about 100 mole percent of the monomer is used.

5. The method of claim 4 wherein from about 5 to about 25 mole percent of photoactive site containing monomers are used.

6. The method of claim 1 wherein the polymer is formed from monomers including at least one monomer having at least one photoactive site or precursor and three or more trifluorovinyl groups or is polymerized in a system containing with a comonomer having at least three or more trifluorovinyl groups in sufficient quantity to result in a thermoset polymer.

7. The method of claim 1 wherein the polymer is formed from monomers having two perfluorovinyl groups and at least one photoactive site or precursor optionally with different monomers having at least two perfluorovinyl groups which polymer is irradiated to form a crosslinked polymer.

8. The method of claim 1 wherein the polymer is applied as a polymer in a liquid media having a molecular weight near the gel point of the polymer and liquid media, but remaining processable.

9. The method of claim 8 wherein the weight average molecular weight is about 5,000 to 500,000.

10. The method of claim 9 wherein the weight average molecular weight is from about 10,000 to about 300,000.

11. The method of claim 1 wherein the polymer is applied in a liquid media and the polymer has a weight average molecular weight greater than about 20,000.

12. The method of claim 11 wherein the polymer is applied in a liquid media and the polymer has a weight average molecular weight greater than about 60,000.

13. The method of claim 1 wherein the incident photonic radiation is of a wavelength of from about 250 nm to about 500 nm.

14. The method of claim 13 wherein the incident photonic radiation is of a wavelength of about 405–436 nm, about 300–365 nm, or about 254–280 nm.

15. The method of claim 15 wherein photosensitizer compounds are also used with the polymer in a quantity sufficient to increase the effect wavelength of the incident photonic radiation.

16. The method of claim 1 wherein crosslinking occurs as a result of incident photonic energy.

17. The method of claim 1 wherein the coating has a thickness from about 0.1 μm to about 2 μm.

18. The method of claim 1 wherein the coating has a thickness from about 0.5 μm to about 5 μm.

19. The method of claim 1 wherein the coating has a thickness from about 5 μm to about 10 μm.

20. The method of claim 1 wherein the coating has a thickness greater than about 10 μm.

21. The method of claim 1 wherein the polymer is applied as a dry film.

22. A method of using a polymer having at least one photoactive site and more than one perfluorocyclobutane group as a negative photoresistant comprising the steps of (1) applying at least one such polymer, which polymer is at least partially soluble or dispersible in a solvent, to a surface or substrate (2) exposing a portion of said polymer to incident photonic radiation such that the exposed portion of the polymer becomes less soluble or dispersible than a remaining unexposed portion, and (3) removing the unexposed portion.

23. The method of claim 22 wherein the polymer is applied dissolved in a solvent comprising at least one ether, ketone, aromatic hydrocarbon, polar aprotic solvent, halocarbon solvent, mesitylene, diglyme, n-methylpyrrolidinone, dimethylformamide, or mixture thereof.

24. The method of claim 22 wherein the polymer is applied to a substrate comprising a metal, silicon, silicon oxide, glass, quartz, polymer, graphite, or combination thereof.

25. The method of claim 22 wherein the polymer is applied in an aqueous medium.

26. The method of claim 22 wherein the photoactive site is selected from at least one chalcone, bischalcone, styrene, cinnamate ester, acrylate, cinnamaldehyde, maleimide, 1,5-aryl-1,4-pentadiene-3-one, naphthoquinone, coumarin, stilbene, (benzylidene)cyclohexanone, bis(benzylidene)cyclohexanones, cinnamylidene cyclohexanone, bis(aryl)nonatetraene, bis(cinnamylidene chclohexanone), 1,5-diaryl-1,4-pentadiene-3-one, cyclohexadienone, acrylate, methacrylate, maleimide, benzophenone, naphthoquinone, polyacetylene, cinnamic acid, β,β'-bis(benzoyl) divinylbenzene, polyenonecycloalkylene, 1-acrylato-2-benzoyloxyethane or combination thereof.

27. The method of claim 22 wherein step (3) comprises immersing the substrate in a bath of the developing solvent for sufficient time to dissolve the uncrosslinked portion of the polymer.

28. The method of claim 22 wherein the surface comprises a glass plate, silicon or silicon oxide wafer, glass bead, copper film, polymer or combination thereof.

29. The method of claim 22 wherein the surface is prepared by washing with soap, rinsing and drying; plasma cleaning; adding an adhesion promoter or a combination thereof.

30. The method of claim 1 wherein the polymer comprises repeating units represented by the formula:

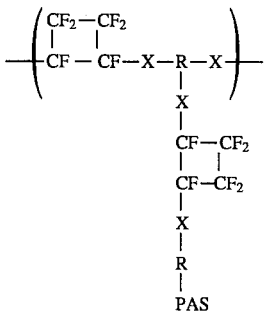

wherein PAS is a photoactive site or photoactive precursor; R is an optionally inertly substituted hydrocarbyl group; and X is a bond or any group which links R and a perfluorocyclobutane group.

31. The method of claim 30 wherein each R is an aromatic hydrocarbyl group of from 6 to about 50 carbon atoms and X includes at least one S, O, Si, N or P atom between R and the perfluorocyclobutane group.

32. The method of claim 1 wherein the polymer is a reaction product of compounds of Formula XIII PAS—R(—X—CF=CF$_2$)$_t$ wherein PAS is a photoactive site or photoactive precursor, R is an optionally inertly substituted hydrocarbyl group, X is a bond or linking group which links R and a perfluorovinyl group, and t is 1, reacted or copolymerized with 1,1,1-tris (4'-trifluoroethenyloxy phenyl)ethane, (1,3,5-tris(2-(4-trifluoroethenyloxy)phenylene)-2-propyl)benzene), the trifluorovinyl etherified Novolac polyphenolic compounds, or mixtures thereof.

33. The method of claim 1 wherein the polymer is prepared from monomers comprising those of the formula $$CF_2=CF_2-X-\underset{(PAS)_r}{R''}-(X-CF=CF_2)_q \qquad \text{(Formula V)}$$

wherein X is a bond or linking group which links R" and a perfluorovinyl group; R" is an unsubstituted or inertly substituted hydrocarbyl group substituted with PAS which is a photoactive site or precursor; q is an integer of from 0 to about 4; and r is an integer from 1 to about 4.

34. The method of claim 1 wherein the polymer is prepared from monomers comprising those of the formula

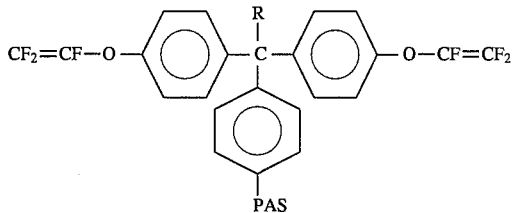

wherein PAS is a photoactive site or photoactive precursor and R is an unsubstituted or inertly substituted hydrocarbyl group.

35. The method of claim 1 wherein the polymer comprises at least one reaction product of a compound having at least three trifluorovinyl groups with 1-acryloxy-2-(4-trifluoroethenoxy)benzoyloxyethane; 1-methacryloxy-2-(4-trifluoroethenoxy) benzoyloxyethane, or mixtures thereof.

36. The method of claim 1 wherein the photoactive sites are n the polymer backbone.

37. The method of claim 36 wherein the polymer is prepared from monomers comprising those of a formula:

CF$_2$=CF—X—PAS—(X—CF=CF$_2$)$_q$ (Formula IV)

wherein PAS is a photoactive site or photoactive precursor; X is any bond or group which links PAS and the perfluorovinyl group; and q is an integer of from 0 to about 4.

38. The method of claim 1 wherein the polymer comprises at least one of 4,4'-bis(trifluoroethenyloxy)-α-methylstilbene, 1,5-bis( 4-trifluoroethenyloxyphenyl)- 1,4-pentadiene-3-one; β-( 4-trifluoroethenyloxybenzylidene)-4-trifluoroethenyloxyacetophenone; 1,3-( 4-dimethylaminobenzylidene)-4-trifluoroethenyloxy-acetophenone; β-(4-methoxybenzylidene)-4-trifluoroethenyloxyacetophenone or mixtures thereof.

39. The method of claim 38 wherein the polymer is a copolymerization product also comprising 1,1,1-tris( 4-trifluoroethenyloxyphenyl)ethane, 4,4'-bis(trifluoroethenyloxy)biphenyl or mixtures thereof.

40. The method of claim 1 wherein the polymer has at least one photoactive site or photoactive precursor which is an unsubstituted or inertly substituted stilbene, styrene, 1-aryl propenyl, bischalcone, chalcone, coumarin, (benzylidene)cyclohexanone, bis(benzylidene)cyclohexanone, cinnamylidene cyclohexanone, bis(aryl)nonatetraene, bis-(cinnamylidene cyclohexanone), 1,5-diaryl- 1,4-pentadiene-3-one, cyclohexadienone, acrylate, methacrylate, maleimide, naphthoquinone, polyacetylene, cinnamic acid, cinnamate ester, cinnamaldehyde, β,β'-bis(benzoyl) divinylbenzene, benzophenone or combination thereof.

41. The method of claim 1 wherein the polymer is prepared from monomers selected from 4,4'-bis(trifluoroethenyloxy)-α-methylstilbene, 1,5-bis(4-trifluoroethenyloxyphenyl)-1,4-pentadiene-3-one; β-( 4-trifluoroethenyloxybenzylidene)-4-trifiuoroethenyloxyacetophenone; β-( 4-dimethylaminobenzylidene)-4-trifluoroethenyloxy-acetophenone; β-( 4-methoxybenzylidene)-4-trifluoroethenyloxyacetophenone.

42. The method of claim 1 wherein the polymer is prepared from monomers selected from a perfluoroethenyloxy-substituted acetophenone and an aldehyde.

43. The method of claim 42 wherein the acetophenone is substituted with at least one cyano, nitro, sulfonate ester, sulfonamide, trifluoromethyl, carboxylic ester, aldehyde, ketone, or halo group, or the aldehyde is a benzaldehyde substituted with at least one tertiary amine, hydroxy group, ether, or alkoxy group para to the aldehyde or propenaldehyde group.

44. The method of claim 1 wherein the polymer is prepared from at least one monomer selected from β-(4-hydroxybenzylidene)- 4-(trifluoroethenyloxy)acetophenone, β-(4-Acetylbenzylidene)- 4-(trifluoroethenyloxy)acetophenone, β-(4-Acetyloxybenzylidene)- 4-(trifluoroethenyloxy)acetophenone, β-(4-aminobenzylidene)- 4-(trifluoroethenyloxy)acetophenone, β-(4-carboxybenzylidene)-4-(trifluoroethenyloxy)acetophenone, β-(4-isocyanatobenzylidene)- 4-(trifluoroethenyloxy)acetophenone, β-(4-chlorocarboxybenzylidene)- 4-(trifluoroethenyloxy)acetophenone, β-(4-carboxymethylbenzylidene)- 4-(trifluoroethenyloxy)acetophenone, β-(4-carboxyethylbenzylidene)- 4-(trifluoroethenyloxy)acetophenone, 4-hydroxy-β-( 4-trifluoroethenyloxybenzylidene)acetophenone, 4-amino-β-( 4-trifluoroethenyloxybenzylidene)acetophenone, 4-carboxy-β-( 4-trifluoroethenyloxybenzylidene)acetophenone, 4-chlorocarboxy-β-( 4-trifluoroethenyloxybenzylidene)acetophenone, 4-isocyanato-β-( 4-trifluoroethenyloxybenzylidene)acetophenone, 4-carboxymethyl-β-( 4-trifluoroethenyloxybenzylidene)acetophenone, 4-carboxyethyl-β- 4-(trifluoroethenyloxybenzylidene)acetophenone, 1-(4-hydroxyphenyl)-2-( 4-trifluoroethenyloxyphenyl)-1-propene, 2-(4-hydroxyphenyl)-1-( 4-trifluoroethenyloxyphenyl)-1-propene, 1-(4-aminophenyl)-2-( 4-trifluoroethenyloxyphenyl)-1-propene, 2-(4-aminophenyl)-1-( 4-trifluoroethenyloxyphenyl)-1-propene, 1-(4-carboxyphenyl)-2-( 4-trifluoroethenyloxyphenyl)-1-propene, 2-(4-carboxyphenyl)-1-( 4-trifluoroethenyloxyphenyl)-1-propene, 1-(4-chlorocarboxyphenyl)-2-( 4-trifluoroethenyloxyphenyl)-1-propene, 2-(4-chlorocarboxyphenyl)-1-( 4-trifluoroethenyloxyphenyl)-1-propene, 1-(4-isocyanatophenyl)-2-( 4-trifluoroethenyloxyphenyl)-1-propene, 2-(4-isocyanatophenyl)-1-( 4-trifluoroethenyloxyphenyl)-1-propene, 1-(4-carboxymethylphenyl)-2-( 4-trifluoroethenyloxyphenyl)-1-propene, 2-(4-carboxymethylphenyl)-1-( 4-trifluoroethenyloxyphenyl)-1-propene, 4-hydroxy- 4'-trifluoroethenyloxystilbene, 4-aminophenyl-4'-trifluoroethenyloxystilbene, 4-carboxyphenyl-4'-trifluoroethenyloxystilbene, 4-isocyanato- 4'-trifluoroethenyloxystilbene, 4-carboxymethyl- 4'-trifluoroethenyloxystilbene, 5-hydroxy-8-trifluoroethenyloxynaphthoquinone, 1-(4-hydroxyphenyl)-5-( 4-trifluoroethenyloxyphenyl)-1,4-pentadien-3-one, 1-(4-aminophenyl)-5-( 4-trifluoroethenyloxyphenyl)-1,4-pentadien-3-one, 1-(4-carboxyphenyl)-5-( 4-trifluoroethenyloxyphenyl)-1,4-pentadien-3-one, 1-( 4-carboxymethylphenyl)-5-(4-trifluoroethenyloxyphenyl)-1,4-pentadien-3-one, 1-(4-isocyanatophenyl)-5-(4-trifluoroethenyloxyphenyl)-1,4-pentadien-3-one, 5-hydroxy-8-trifluoroethenyloxycoumarin, 8-hydroxy-5-trifluoroethenyloxycoumarin, 5-amino-8-trifluoroethenyloxycoumarin, 8-amino-5-trifluoroethenyloxycoumarin, 5-isocyanato- 8-trifluoroethenyloxycoumarin, 8-isocyanato-5-trifluoroethenyloxycoumarin, 2-(4-hydroxybenzylidene)-6-( 4-trifluoroethenyloxybenzylidene)cyclohexanone, 2-(4-hydroxybenzylidene)-6-(4-trifluoroethenyloxybenzylidene)-4-methylcyclohexanone, 2-( 4-aminobenzylidene)-6-(4-trifluoroethenyloxybenzylidene)cyclohexanone, 2-(4-aminobenzylidene)-6-(4-trifluoroethenyloxybenzylidene)- 4-methylcyclohexanone, 2-(4-carboxymethylbenzylidene)-6-( 4-trifluoroethenyloxybenzylidene)cyclohexanone, 2-( 4-carboxymethylbenzylidene)-6-(4-trifluoroethenyloxybenzylidene)- 4-methylcyclohexanone, 2-(4-isocyanatobenzylidene)-6-( 4-trifluoroethenyloxybenzylidene)cyclohexanone, 2-( 4-isocyanatobenzylidene)-6-(4-trifluoroethenyloxybenzylidene)-4-methylcyclohexanone, 2-(4-chlorocarboxybenzylidene)-6-( 4-trifluoroethenyloxybenzylidene)cyclohexanone, and 2-( 4-chlorocarboxybenzylidene)-6-(4-trifluoroethenyloxybenzylidene)- 4-methylcyclohexanone.

45. The method of claim 1 wherein the polymer is prepared from at least one monomer selected from 1-(4-acroyloxyphenyl)-1,1-bis( 4-trifluoroethenyloxyphenyl)ethane, 1-(4-methacroyloxyphenyl)-1,1-bis( 4-trifluoroethenyloxyphenyl)ethane, 1-(4-acroylphenyl)-1,1-bis( 4-trifluoroethenyloxyphenyl)ethane, 1-(4-methacroylphenyl)-1,1-bis( 4-trifluoroethenyloxyphenyl)ethane, 4-(1,1-bis( 4-trifluoroethenyloxyphenyl)ethyl)-β-(benzylidene)acetophenone, 4-( 1,1-bis(4-trifluoroethenyloxyphenyl)ethyl)-β-(4-dimethylaminobenzylidene) acetophenone, 4-(1,1-bis(4-trifluoroethenyloxyphenyl)ethyl)-β-( 4-methoxybenzylidene)acetophenone, 4-(1,1-bis( 4-trifluoroethenyloxyphenyl)ethyl)-β-(4-trifluoromethylbenzylidene) acetophenone, 4-(1,1-bis(4-trifluoroethenyloxyphenyl)ethyl)-β-( 4-carboxymethylbenzylidene)acetophenone, 4-(1,1-bis( 4-trifluoroethenyloxyphenyl)ethyl)-β-(4-nitrobenzylidene)acetophenone, 4-(1,1-bis(4-trifluoroethenyloxyphenyl)ethyl)-β-( 4-chlorobenzylidene)acetophenone, 4-(1,1-bis( 4-trifluoroethenyloxyphenyl)ethyl)-β-(4-fluorobenzylidene)acetophenone, 4-(1,1-bis(4-trifluoroethenyloxyphenyl)ethyl)-β-( 4-acetylbenzylidene)acetophenone, 4-(1,1-bis( 4-trifluoroethenyloxyphenyl)ethyl)-β-( 4-cyanobenzylidene)acetophenone, 4-(1,1-bis(4-trifluoroethenyloxyphenyl)ethyl)styrene, 4-(1,1-bis( 4-trifluoroethenyloxyphenyl)ethyl)-N-phenyl maleimide, 1-(4-(1,1-bis( 4-trifluoroethenyloxyphenyl)ethyl)phenyl)-5-phenyl-1,4-pentadiene-3-one, 1-(4-(1,1-bis(4-trifluoroethenyloxyphenyl)ethyl)phenyl)-5-( 4-(dimethylamino)phenyl)-1,4-pentadiene-3-one, 1-(4-(1,1-bis( 4-trifluoroethenyloxyphenyl)ethyl)phenyl)-5-(4-methoxyphenyl)- 1,4-pentadiene-3-one, 1-(4-(1,1-bis(4-trifluoroethenyloxyphenyl)ethyl)phenyl)-5-(4-(carboxymethyl)phenyl)-1,4-pentadiene-3-one, 1-(4-(1,1-bis( 4-trifluoroethenyloxyphenyl)ethyl)phenyl)-5-(4-(carboxyethyl)phenyl)- 1,4-pentadiene-3-one, 1-(4-(1,1-bis(4-trifluoroethenyloxyphenyl)ethyl)phenyl)- 5-(4-(trifluoromethyl)phenyl)-1,4-pentadiene-3-one, 1-(4-(1,1-bis( 4-trifluoroethenyloxyphenyl)ethyl)phenyl)-5-(4-nitrophenyl)-1,4-pentadiene- 3-one, 1-(4-(1,1-bis(4-trifluoroethenyloxyphenyl)ethyl)phenyl)-5-( 4-chlorophenyl)-1,4-pentadiene-3-one, 1-(4-(1,1-bis( 4-trifluoroethenyloxyphenyl)ethyl)phenyl)-5-(4-fluorophenyl)-1,4-pentadiene-3-one, 1-(4-(1,1-bis(4-trifluoroethenyloxyphenyl)ethyl)phenyl)-5-( 4-acetophenyl)-1,4-pentadiene-3-one, 1-(4-(1,1-bis( 4-trifluoroethenyloxyphenyl)ethyl)phenyl)-5-(4-cyanophenyl)-1,4-pentadiene-3-one, 4-(1,1-bis(4-trifluoroethenyloxyphenyl)ethyl)phenyl acetylene, 4-(1,1-bis(4-trifluoroethenyloxyphenyl)ethyl)phenyl buta-1,3-diyne, 4-(1,1-bis(4-trifluoroethenyloxyphenyl)ethyl)phenyl hexa-1,3,5-triyne, 4-(1,1-bis(4-trifluoroethenyloxyphenyl)ethyl)phenyl octa-1,3,5,7-tetrayne, 4-(1,1-bis(4-trifluoroethenyloxyphenyl)ethyl)phenyl-1,3,5,7,9-pentayne, 6-(4-(1,1-bis(4-trifluoroethenyloxyphenyl)ethyl)phenoxy)naphthoquinone, 6-( 4-(1,1-bis(4-trifluoroethenyloxyphenyl)ethyl)phenoxy)coumarin, 7-(4-(1,1-bis(4-trifluoroethenyloxyphenyl)ethyl)phenoxy)coumarin, 2-(4-( 1,1-bis(trifluoroethenyloxyphenyl)ethyl)benzylidene)cyclohexanone, 2-(4-(4-(1,1-bis(trifluoroethenyloxyphenyl)ethyl)phenoxy)benzylidene) cyclohexanone, 1-acroyloxy-2-(2-trifluoroethenyloxy)benzoyloxyethane, 1-methacroyloxy-2-(4-trifluoroethenyloxy)benzoyloxyethane, N-( 4-trifluoroethenyloxyphenyl)acrylamide, N-( 4-trifluoroethenyloxyphenyl)methacrylamide, 4-trifluoroethenyloxyphenyl acrylate, 4-trifluoroethenyloxyphenyl methacrylate, N-( 4-trifluoroethenyloxyphenyl)maleimide, N-( 4-trifluoroethenyloxybenzoyl)maleimide, β-(4-methoxybenzylidene)-4-(trifluoroethenyloxy)acetophenone, β-(4-dimethylaminobenzylidene)- 4-(trifluoroethenyloxy)acetophenone, β-(4-carboxymethylbenzylidene)- 4-(trifluoroethenyloxy)acetophenone, β-(4-carboxyethylbenzylidene)-4-(trifluoroethenyloxy)acetophenone, β-(4-nitrobenzylidene)- 4-(trifluoroethenyloxy)acetophenone, β-(4-chlorobenzylidene)- 4-(trifluoroethenyloxy)acetophenone, β-(4-fluorobenzylidene)- 4-(trifluoroethenyloxy)acetophenone, β-(4-acetylbenzylidene)- 4-(trifluoroethenyloxy)acetophenone, β-(4-cyanobenzylidene)- 4-(trifluoroethenyloxy)acetophenone, β-(3-trifluoromethylbenzylidene)- 4-(trifluoroethenyloxy)acetophenone, β-(4-trifluoromethylbenzylidene)-4-(trifluoroethenyloxy)acetophenone, β-(4-trifluoroethenyloxybenzylidene)acetophenone, 4-methoxy-β-( 4-trifluoroethenyloxybenzylidene), 4-dimethylamino-β-( 4-trifluoroethenyloxybenzylidene)acetophenone, 4-carboxymethyl-β-( 4-trifluoroethenyloxybenzylidene)acetophenone, 4-carboxyethyl-β-( 4-trifluoroethenyloxybenzylidene)acetophenone, 4-chloro-β-( 4-trifluoroethenyloxybenzylidene)acetophenone, 4-nitro-β-( 4-trifluoroethenyloxybenzylidene)acetophenone, 4-fluoro-β-( 4-trifluoroethenyloxybenzylidene)acetophenone, 4-acetyl-β-( 4-trifluoroethenyloxybenzylidene)acetophenone, 4-cyano-β-( 4-trifluoroethenyloxybenzylidene)acetophenone, 4-trifluoromethyl-β-( 4-trifluoroethenyloxybenzylidene)acetophenone, 3-trifluoromethyl-β-( 4-trifluoroethenyloxybenzylidene)acetophenone, 4-trifluoroethenyloxycinnamaldehyde, 4-trifluoroethenyloxycinnamic acid, 4-trifluoroethenyloxycinnamic acid, methyl ester, 4-trifluoroethenyloxycinnamic acid, ethyl ester, 4-trifluoroethenyloxycinnamic acid, isopropyl ester, 4-trifluoroethenyloxycinnamic acid, phenyl ester, 1-( 4-trifluoroethenyloxyphenyl)-propen-1-one, 1-(4- trifluoroethenyloxyphenyl)-1-buten-3-one, 5-(trifluoroethenyloxy)naphthoquinone, 6-(trifluoroethenyloxy)naphthoquinone, 5-( 4-(trifluoroethenyloxy)benzoyloxy)naphthoquinone,6-( 4-(trifluoroethenyloxy)benzoyloxy)naphthoquinone, 5-(trifluoroethenyloxy)coumarin, 6-(trifluoroethenyloxy)coumarin, 7-(trifluoroethenyloxy)coumarin, 8-(trifluoroethenyloxy)coumarin, 5-( 4-(trifluoroethenyloxy)benzoyloxy)coumarin, 6-( 4-(trifluoroethenyloxy)benzoyloxy)coumarin, 7-( 4-(trifluoroethenyloxy)benzoyloxy)coumarin, 8-( 4-(trifluoroethenyloxy)benzoyloxy)coumarin, 2-( 4-trifluoroethenyoxylbenzylidene)cyclohexanone, 1-( 4-trifluoroethenyloxyphenyl)-5-phenyl-1,4-pentadiene-3-one, 1-( 4-trifluoroethenyloxyphenyl)-5-(4-(dimethylamino)phenyl)-1,4-pentadiene- 3-one, 1-(4-trifluoroethenyloxyphenyl)-5-(4-methoxyphenyl)-1,4-pentadiene-3-one, 1-(4-trifluoroethenyloxyphenyl)-5-(4-(carboxymethyl)phenyl)- 1,4-pentadiene-3-one, 1-(4-trifluoroethenyloxyphenyl)-5-(4-(carboxyethyl)phenyl)-1,4-pentadiene-3-one, 1-( 4-trifluoroethenyloxyphenyl)-5-(4-(trifluoromethyl)phenyl)-1,4-pentadiene- 3-one, 1-(4-trifluoroethenyloxyphenyl)-5-(3-(trifluoromethyl)phenyl)- 1,4-pentadiene-3-one, 1-(4-trifluoroethenyloxyphenyl)-5-(4-nitrophenyl)- 1,4-pentadiene-3-one, 1-(4-trifluoroethenyloxyphenyl)-5-(4-chlorophenyl)- 1,4-pentadiene-3-one, 1-(4-trifluoroethenyloxyphenyl)-5-(4-fluorophenyl)- 1,4-pentadiene-3-one, 1-(4-trifluoroethenyloxyphenyl)-5-(4-acetophenyl)- 1,4-pentadiene-3-one, 1-(4-methoxyphenyl)-2-(4-trifluoroethenyloxyphenyl)- 1-propene, 2-(4-methoxyphenyl)-1 o(4-trifluoroethenyloxyphenyl)-1-propene, 1-(4-dimethylaminophenyl)-2-(4-trifluoroethenyloxyphenyl)-1-propene, 2-(4-dimethylaminophenyl)-1-(4-trifluoroethenyloxyphenyl)-1-propene, 1-( 4-carboxymethylphenyl)-2-(4-trifluoroethenyloxyphenyl)-1-propene, 2-( 4-carboxymethylphenyl)-1-(4-trifluoroethenyloxyphenyl)-1-propene, 1-( 4-chlorophenyl)-2-(4-trifluoroethenyloxyphenyl)-1-propene, 2-( 4-chlorophenyl)-1-(4-trifluoroethenyloxyphenyl)-1-propene, 1-(4-nitrophenyl)-2-(4-trifluoroethenyloxyphenyl)-1-propene, 2-(4-nitrophenyl)-1-( 4-trifluoroethenyloxyphenyl)-1-propene, 1-(4-fluorophenyl)-2-( 4-trifluoroethenyloxyphenyl)-1-propene, 2-(4-fluorophenyl)-1-( 4-trifluoroethenyloxyphenyl)-1-propene, 1-(4-cyanophenyl)-2-( 4-trifluoroethenyloxyphenyl)-1-propene, 2-(4-cyanophenyl)-1-( 4-trifluoroethenyloxyphenyl)-1-propene, 2-(4-acetylphenyl)-1-( 4-trifluoroethenyloxyphenyl)-1-propene, 2-(4-acetylphenyl)-1-( 4-trifluoroethenyloxyphenyl)-1-propene, 4-methoxy- 4'-trifluoroethenyloxystilbene, 4-dimethylaminophenyl- 4'-trifluoroethenyloxystilbene, 4-carboxymethylphenyl- 4'-trifluoroethenyloxystilbene, 4-carboxyethylphenyl- 4'-trifluoroethenyloxystilbene, 4-nitro-4'-trifluoroethenyloxystilbene, 4-chloro-4'-trifluoroethenyloxystilbene, 4-fluoro-4'-trifluoroethenyloxystilbene, 4-cyano-4'-trifluoroethenyloxystilbene, 4-acetyl-4'-trifluoroethenyloxystilbene, 4-trifluoromethyl- 4'-trifluoroethenyloxystilbene, 1-(4-dimethylaminophenyl)-5-( 4-trifluoroethenyloxyphenyl)-1,4-pentadiene-3-one, 1-(4-methoxyphenyl)-5-(4-trifluoroethenyloxyphenyl)-1,4-pentadiene-3-one, β-cinnamylidene-4-trifluoroethenyloxyacetophenone, β-(4'-dimethylaminocinnamylidene)- 4-trifluoroethenyloxyacetophenone, β-(2'-methoxycinnamylidene)- 4-trifluoroethenyloxyacetophenone, β-(4'-methoxycinnamylidene)- 4-trifluoroethenyloxyacetophenone, 4-(1,1-bis( 4-trifluoroethenyloxyphenyl)ethyl)-β-(benzylidene)acetophenone, 4-(1,1-bis(4-trifluoroethenyloxyphenyl)ethyl)-β-( 4'-methoxybenzylidene)acetophenone, 4-(1,1-bis( 4-trifluoroethenyloxyphenyl)ethyl)-β-( 4'-dimethylaminobenzylidene)acetophenone, 4-(1,1-bis( 4-trifluoroethenyloxyphenyl)ethyl)-β-(4'-cyanobenzylidene)acetophenone, 4-(1,1-bis(4-trifluoroethenyloxyphenyl)ethyl)-β-( 4'-nitrobenzylidene)acetophenone, 4-(1,1-bis( 4-trifluoroethenyloxyphenyl)ethyl)-β-(cinnamylidene)acetophenone, 4-(1,1-bis(4-trifluoroethenyloxyphenyl) ethyl)-β-( 2'-methoxycinnamylidene)acetophenone, 4-(1,1-bis( 4-trifluoroethenyloxyphenyl)ethyl)-β-( 4'-methoxycinnamylidene)acetophenone, 4-(1,1-bis( 4-trifluoroethenyloxyphenyl)ethyl)-β-( 4'-dimethylaminocinnamylidene)acetophenone, 4-(1,1-bis( 4-trifluoroethenyloxyphenyl)ethyl)-β-(4'-nitrocinnamylidene)acetophenone, 1,1-bis(4-trifluoroethenyloxyphenyl)-1-(4-(3-(2-furanyl)-2-propene-1-onyl)phenyl)ethane, 1,1-bis(4-trifluoroethenyloxyphenyl)-1-(4-(5-( 2-furanyl)-2,4-pentadiene-1-onyl)phenyl)ethane, 3,5-bis(trifluoroethenyloxy) -β-(benzylidene)acetophenone, 3,5-bis(trifluoroethenyloxy)-β-( 4'-methoxybenzylidene)acetophenone, 3,5-bis(trifluoroethenyloxy)-β-( 4'-dimethylaminobenzylidene)acetophenone, 3,5-bis(trifluoroethenyloxy)-β-(4'-cyanobenzylidene)acetophenone, 3,5-bis(trifluoroethenyloxy)-β-( 4'-nitrobenzylidene)acetophenone, 3,5-bis(trifluoroethenyloxy)-β-(cinnamylidene)acetophenone, 3,5-bis(trifluoroethenyloxy)-β-( 2'-methoxycinnamylidene)acetophenone, 3,5-bis(trifluoroethenyloxy)-β-( 4'-methoxycinnamylidene)acetophenone, 3,5-bis(trifluoroethenyloxy)-β-(4'-dimethylaminocinnamylidene)acetophenone, 3,5-bis(trifluoroethenyloxy)-β-(nitrocinnamylidene)acetophenone, 3,5-bis(trifluoroethenyloxy)-1-(3-(2-(furanyl)-2-propene-1-onyl)benzene, 3,5-bis(trifluoroethenyloxy)-1-(5-(2-(furanyl)-2,4-pentadiene-1-onyl)benzene, 2-(3-phenyl-2-propene-1-onyl)-9,9-bis(4-trifluoroethenyloxyphenyl)fluorene, 2-(3-(4-methoxyphenyl)-2-propene-1-onyl)-9,9-bis( 4-trifluoroethenyloxyphenyl)fluorene, 2-(3-(2-methoxyphenyl)-2-propene- 1-onyl)-9,9-bis(4-trifluoroethenyloxyphenyl)fluorene, 2-(3-( 4-dimethylaminophenyl)-2-propene-1-onyl)-9,9-bis( 4-trifluoroethenyloxyphenyl)fluorene, 2-(3-(4-cyanophenyl)-2-propene- 1-onyl)-9,9-bis(4-trifluoroethenyloxyphenyl)fluorene, 2-(3-(4-nitrophenyl)-2-propene-1-onyl)-9,9-bis(4-trifluoroethenyloxyphenyl)fluorene, 2,7-bis( 3phenyl-2-propene-1-onyl)-9,9-bis(4-trifluoroethenyloxyphenyl)fluorene, 2,7-bis(3-(4-methoxyphenyl)-2-propene-1-onyl)-9,9-bis( 4-trifluoroethenyloxyphenyl)fluorene, 2,7-bis(3-(2-methoxyphenyl)- 2-propene-1-onyl)-9,9-bis(4-trifluoroethenyloxyphenyl)fluorene, 2,7-bis(3-( 4-dimethylaminophenyl)-2-propene-1-onyl)-9,9-bis( 4-trifluoroethenyloxyphenyl)fluorene, 2,7-bis(3-(4-cyanophenyl)-2-propene- 1-onyl)-9,9-bis(4-trifluoroethenyloxyphenyl)fluorene, 2,7-bis(3-( 4-nitrophenyl)-2-propene-1-onyl)-9,9-bis( 4-trifluoroethenyloxyphenyl)fluorene, 2-(5-phenyl-2,4-pentadiene-1-onyl)-9,9-bis(4-trifluoroethenyloxyphenyl)fluorene, 2-(5-(4-methoxyphenyl)- 2,4-pentadiene-1-onyl)-9,9-bis(4-trifluoroethenyloxyphenyl)fluorene, 2-(5-( 2-methoxyphenyl)-2,4-pentadiene-1-onyl)-9,9-bis( 4-trifluoroethenyloxyphenyl)fluorene, 2-(5-(4-dimethylaminophenyl)- 2,4-pentadiene-1-onyl)-9,9-bis(4-trifluoroethenyloxyphenyl)fluorene, 2-(5-( 4-cyanophenyl)-2,4-pentadiene-1-onyl)-9,9-bis( 4-trifluoroethenyloxyphenyl)fluorene, 2-(5-(4-nitrophenyl)-2,4-pentadiene- 1-onyl)-9,9-bis(4-trifluoroethenyloxyphenyl)fluorene, 2,7-bis(5-phenyl- 2,4-pentadiene-1-onyl)-9,9-bis(4-trifluoroethenyloxyphenyl)fluorene, 2,7-bis(5-(4-methoxyphenyl)-2,4-pentadiene-1-onyl)-9,9-bis( 4-trifluoroethenyloxyphenyl)fluorene, 2,7-bis(5-(4-dimethylaminophenyl)- 2,4-pentadiene-1-onyl)-9,9-bis(4-trifluoroethenyloxyphenyl)fluorene, 2,7-bis(5-(2-dimethylaminophenyl)-2,4-pentadiene-1-onyl)-9,9-bis( 4-trifluoroethenyloxyphenyl)fluorene, 2,7-bis(5-(4-cyanophenyl)- 2,4-pentadiene-1-onyl)-9,9-bis(4-trifluoroethenyloxyphenyl)fluorene, and 2,7-bis(5-(4-nitrophenyl)-2,4-pentadiene-1-onyl)-9,9-bis( 4-trifluoroethenyloxyphenyl)fluorene.

46. The method of claim 1 wherein the polymer is prepared from at least one monomer selected from 4,4'-bis(trifluoroethenyloxy)-α-methylstilbene; 4,4'-bis(trifluoroethenyloxy)stilbene; 4-Trifluoroethenyloxy-β-(4-trifluoroethenyloxybenzylidene)acetophenone; 2,6-bis(4-trifluoroethenyloxybenzylidene)cyclohexanone; 2,6-bis( 4-trifluoroethenyloxybenzylidene)-4-methylcyclohexanone; 1,4-bis(3-( 4-trifluoroethenyloxyphenyl)-2-propene-1-onyl)benzene; 1,3-bis(3-( 4-trifluoroethenyloxyphenyl)-2-propene-1-onyl)benzene; 1,4-bis(3-( 4-trifluoroethenyloxyphenyl)-1-propene-3-onyl)benzene; 1,3-bis(3-( 4-trifluoroethenyloxyphenyl)-1-propene-3-onyl)benzene; 1,5-bis( 4-trifluoroethenyloxyphenyl)-1,4-pentadiene-3-one; 4-Trifluoroethenyloxy-β-(4-trifluoroethenyloxybenzylidene)acetophenone; 4,4'-bis-(trifluoroethenyloxy)stilbene; (4,4'-bis(trifluoroethenyloxy)-β-methylstilbene; β,β'-bis(4-trifluoroethenyloxybenzylidene)- 1,4-diacetylbenzene; β,β'-bis(4-trifluoroethenyloxybenzylidene)- 1,3-diacetylbenzene; β,β'-bis(4-trifluoroethenyloxybenzylidene)- 1,2diacetylbenzene; 5,8-bis(trifluoroethenyloxy)coumarin; 2,6-bis(4,trifluoroethenyloxybenzylidene)cyclohexanone; 2,6-bis(4,trifluoroethenyloxybenzylidene)-4-methylcyclohexanone; 5,8-bis(trifluoroethenyloxy)naphthoquinone; β,β'-bis( 4-trifluoroethenyloxybenzoyl)-1,4-divinylbenzene, and 4,4'-bis(trifluoroethenyloxy)benzophenone.

47. The method of claim 1 wherein the polymer is prepared from at least one monomer selected from 4,4'-bis(2-bromotetrafluoroethoxy)-α-methylstilbene; 4-(2-bromotetrafluoroethoxy)benzaldehyde; 4-( 2-bromotetrafluoroethoxy)acetophenone; and β-(4-( 2-bromotetrafluoroethoxy)benzylidene) -4-( 2-bromotetrafluoroethoxy)acetophenone.

* * * * *

UNITED STATES PATENT AND TRADEMARK OFFICE
CERTIFICATE OF CORRECTION

PATENT NO. : 5,489,623
DATED : February 6, 1996
INVENTOR(S) : David A. Babb; W. Frank Richey; Katherine S. Clement; Eric S. Moyer; Marius W. Sorenson It is certified that error appears in the above-identified patent and that said Letters Patent is hereby corrected as shown below:

Title page, column 2, OTHER PUBLICATIONS, line 12, following <u>Cinnamate).</u> Insert a paragraph Claim 4, column 41, line 19, following <u>about</u> insert - - 1 - -

Claim 15, column 41, line 56, "15" should correctly read - - 1 - -

Claim 38, column 43, line 60, "1,3" should correctly read - - β - -

Signed and Sealed this

Twenty-seventh Day of October, 1998

Attest:

BRUCE LEHMAN

*Attesting Officer*      *Commissioner of Patents and Trademarks*